US007951782B2

(12) United States Patent
Murota et al.

(10) Patent No.: US 7,951,782 B2
(45) Date of Patent: May 31, 2011

(54) COMPOSITION EFFECTIVE TO PREVENT OR TREAT ADULT DISEASE

(75) Inventors: Itsuki Murota, Ibaraki (JP); Tadakazu Tamai, Ibaraki (JP); Takashi Baba, Ibaraki (JP); Kenji Sato, Kyoto (JP)

(73) Assignee: Maruha Nichiro Seafoods, Inc, Tokyo (JP)

( * ) Notice: Subject to any disclaimer, the term of this patent is extended or adjusted under 35 U.S.C. 154(b) by 370 days.

(21) Appl. No.: 12/065,984

(22) PCT Filed: Sep. 28, 2006

(86) PCT No.: PCT/JP2006/319240
§ 371 (c)(1),
(2), (4) Date: Mar. 6, 2008

(87) PCT Pub. No.: WO2007/037297
PCT Pub. Date: Apr. 5, 2007

(65) Prior Publication Data
US 2010/0004182 A1 Jan. 7, 2010

(30) Foreign Application Priority Data
Sep. 29, 2005 (JP) ................. 2005-283585

(51) Int. Cl.
*A61K 38/08* (2006.01)
*A61K 38/06* (2006.01)
*A61K 38/07* (2006.01)
(52) U.S. Cl. ...................... 514/21.8; 514/21.9
(58) Field of Classification Search .................. None
See application file for complete search history.

(56) References Cited

U.S. PATENT DOCUMENTS

| 3,478,146 | A * | 11/1969 | Balassa ........................ 424/548 |
| 6,383,522 | B1 | 5/2002 | Dupont |
| 2002/0012714 | A1 | 1/2002 | Olson |
| 2002/0146462 | A1 | 10/2002 | Dupont |
| 2003/0040475 | A1 | 2/2003 | Toba et al. |
| 2004/0167078 | A1 | 8/2004 | Toba et al. |
| 2005/0222010 | A1 | 10/2005 | Murota et al. |

FOREIGN PATENT DOCUMENTS

| JP | 6-178671 | 6/1994 |
| JP | 11-513990 | 11/1999 |
| JP | 2001-500899 | 1/2001 |
| JP | 2001-1048795 | 2/2001 |
| JP | 2001-231497 | 8/2001 |
| JP | 2002-088098 | 3/2002 |
| JP | 2002-212097 | 7/2002 |
| JP | 2003-246796 | 9/2003 |
| JP | 2003-335698 | 11/2003 |
| JP | 2003-532680 | 11/2003 |
| JP | 2005-154326 | 6/2005 |

OTHER PUBLICATIONS

JP 2005-154326 (translation to English from Japanese). 22 pages.*
"Alloxan Tonyobyo Mouse ni Taisuru Same no Nankotsu Seibun no Eikyo", Kazuhiro Nanado et al., Dai 53 Kai, The Japanese Society of Nutrition and Food Science Taikai Koen Yoshishu, 1999, p. 37, 2D-25p.
International Search Report dated Dec. 26, 2006.
Nobuhiro Yamada, Junkanki Now 12, Doumyakukouka Koushiketsusyo, p. 153, Mar. 15, 1996.
Douck-Choun Park et al: "Enzymatic hydrolysis conditions for preparation of sea cucumber hydrolysates containing chondroitin sulfate." Food Science and Biotechnology 10 (6) 686-689 2001 Correspondence (Reprint) Address, Seon-Bong Kim, Fac. of Food & Biotech., Inst. of Seafood Sci., Pukyong Nat. Univ., Busan 608-737, Korea, Jan. 1, 2001, XP009126245.
European Patent Office issued an European Search Report dated Jan. 28, 2010, Application No. 06810698.8.
Articles of Annual Science Meeting of the Japanese Cancer Association, Aug. 2005, vol. 64, pp. 212-213, PP1-0491.
Abstracts of lectures at Annual Meeting of Japanese Society of Nutrition and Food Science, Apr. 2005, vol. 59, p. 180, 2H-1p.
Abstracts of lectures at Annual Meeting of Japanese Society of Nutrition and Food Science, 2006, vol. 56, p. 186, 2L-15p.
Abstracts of lectures at Meeting of Japan Society for Bioscience, Biotechnology, and Agrochemistry, 2002, vol. 2002, p. 246, 4-3Ba19, 4-3Ba20.
Articles of Annual Meeting of the Japanese Cancer Association, 2001, vol. 60, p. 260, 767.
Abstracts of lectures at Science Meeting of Japanese Society of Veterinary Science, 2000, vol. 130, p. 249, P12-7.
Notice of Rejection in Japanese Patent Application No. 2007-537656 mailed Dec. 7, 2010 with English translation of Notice.

* cited by examiner

*Primary Examiner* — Marcela M Cordero Garcia
(74) *Attorney, Agent, or Firm* — Young & Thompson

(57) ABSTRACT

Disclosed is a composition comprising, as an active ingredient, an enzyme digest that is produced by digesting a basic fraction of an animal-derived cartilage extract with an enzyme. Also disclosed is a polypeptide composition comprising, as an active ingredient, at least one polypeptide selected from specific polypeptides including a polypeptide comprising an amino acid sequence depicted in any one of SEQ ID NOs: 1, 2, 3, 4, 5, 6, 7, 8, 9 and 10.

5 Claims, 16 Drawing Sheets

[Fig.1]
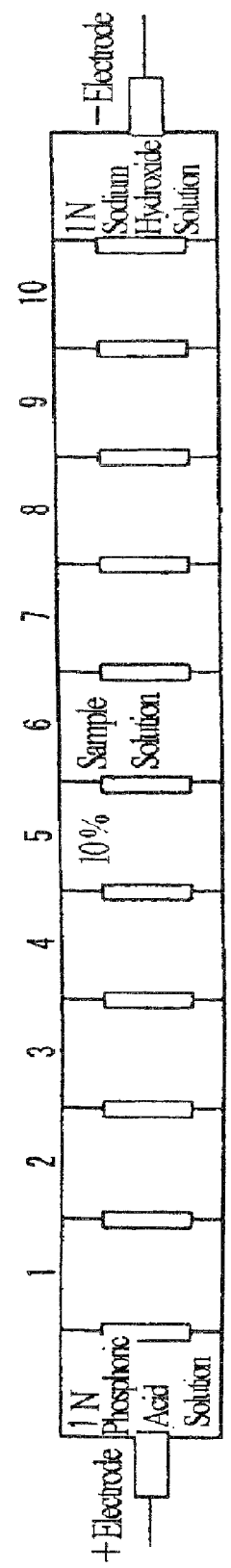

[Fig.2]
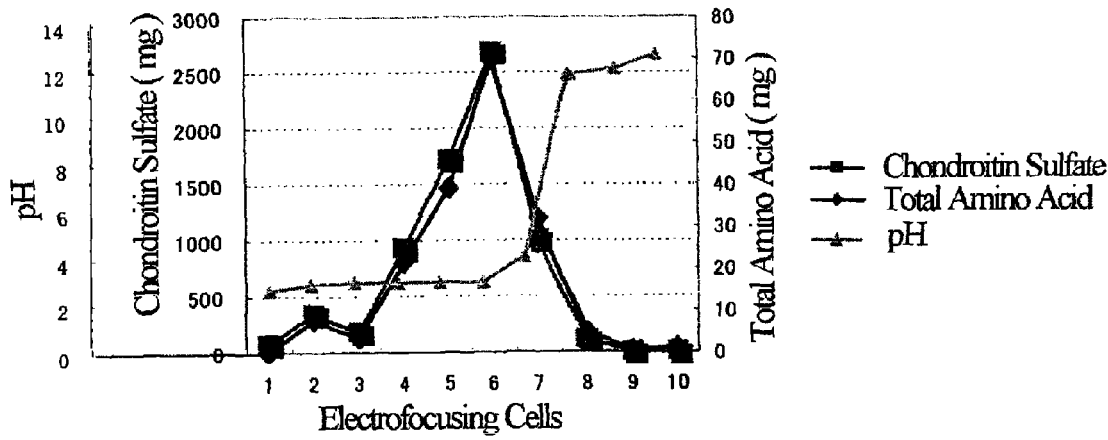
[Fig.3]
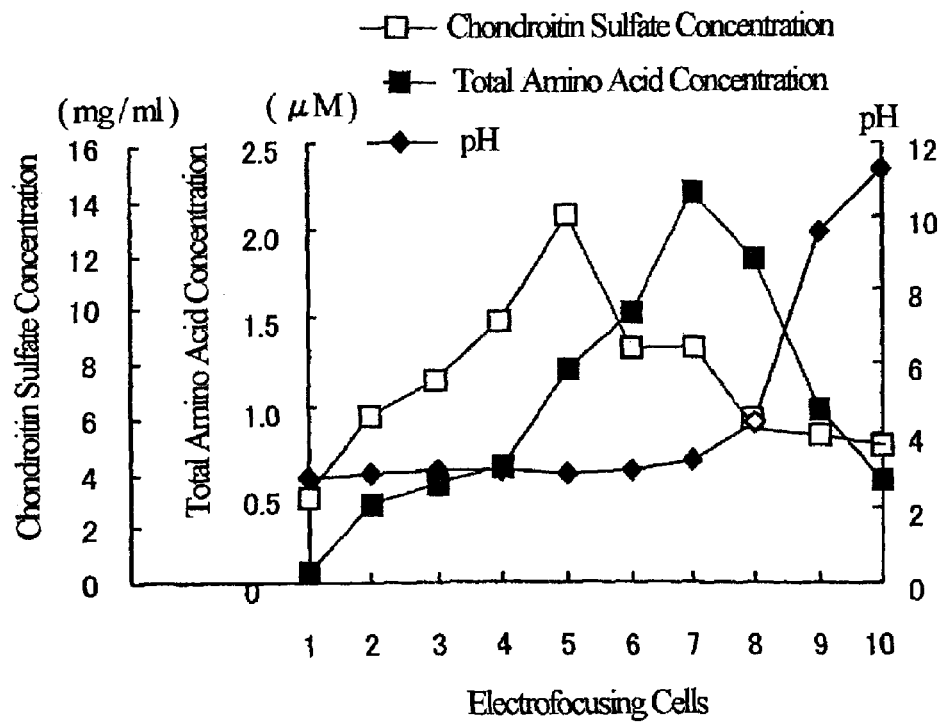

[Fig.4]
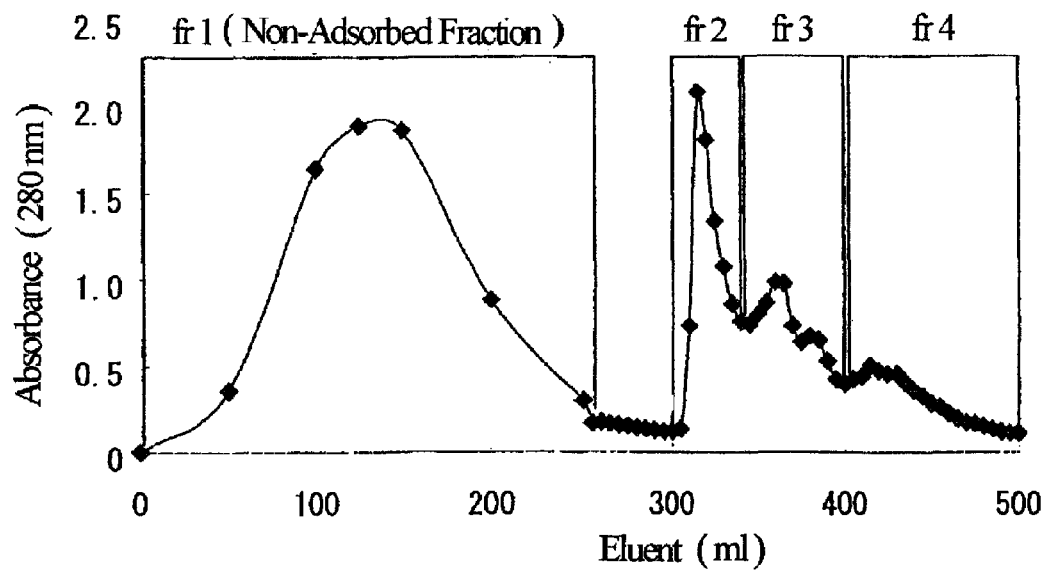
[Fig.5]
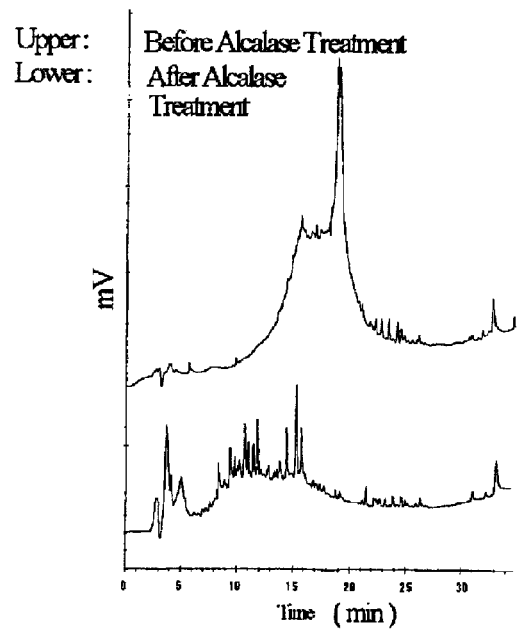

[Fig.6]
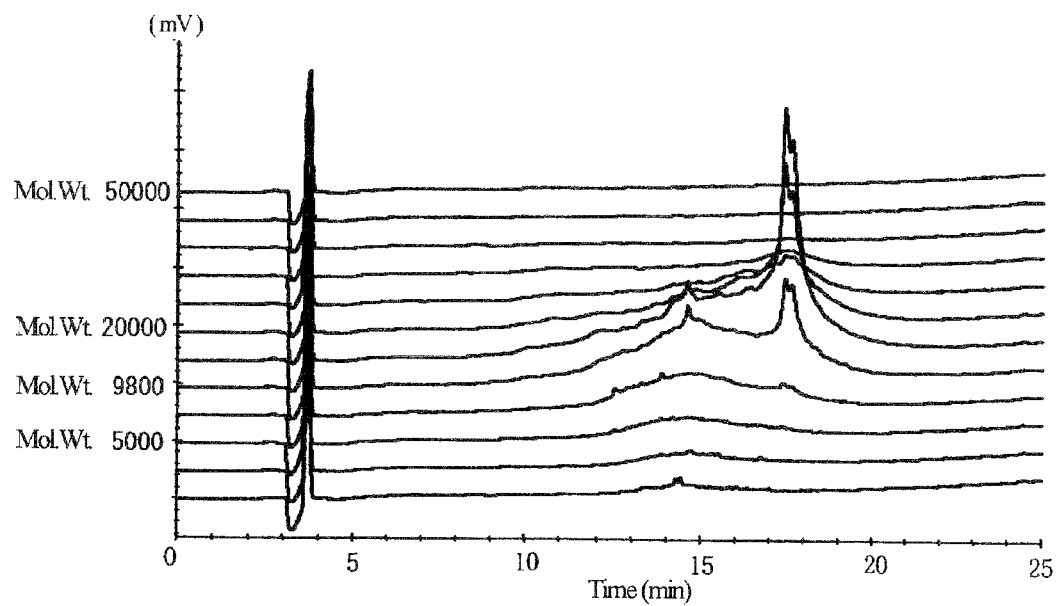
[Fig.7]
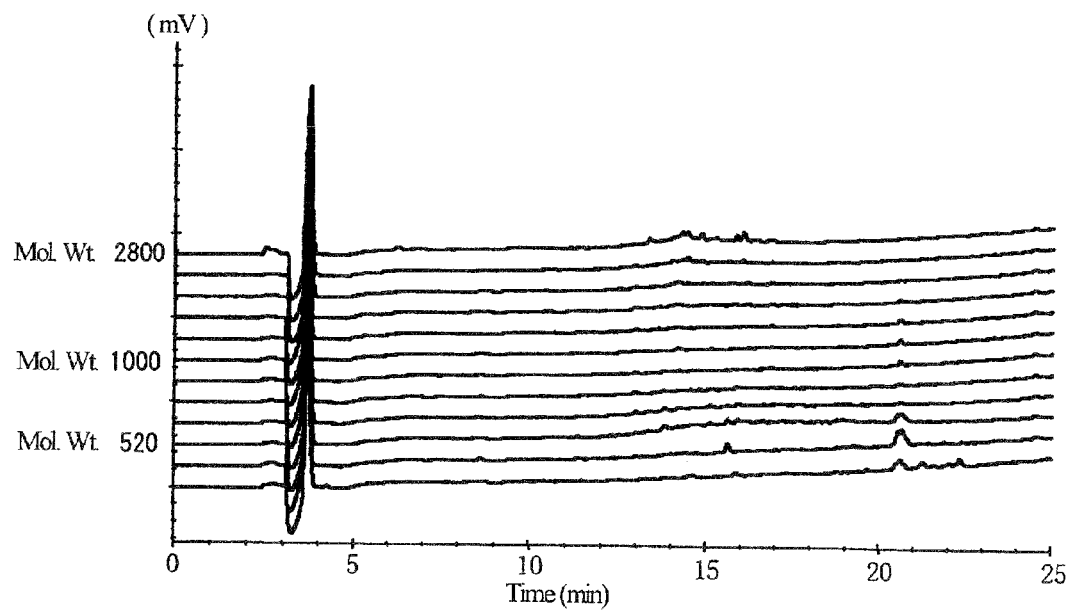

[Fig.8]
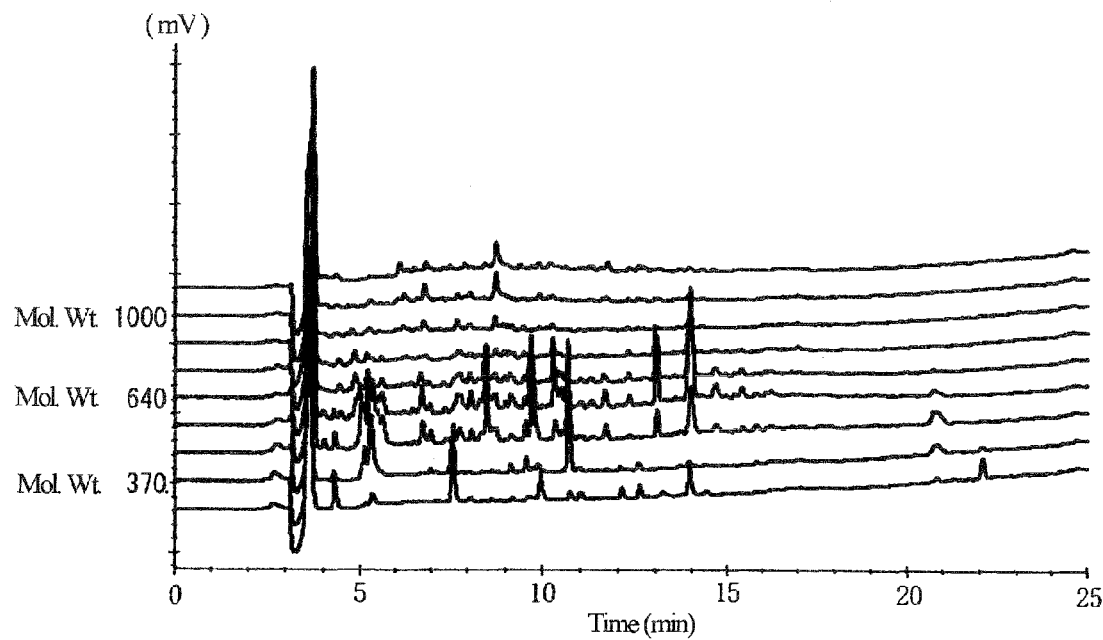
[Fig.9]
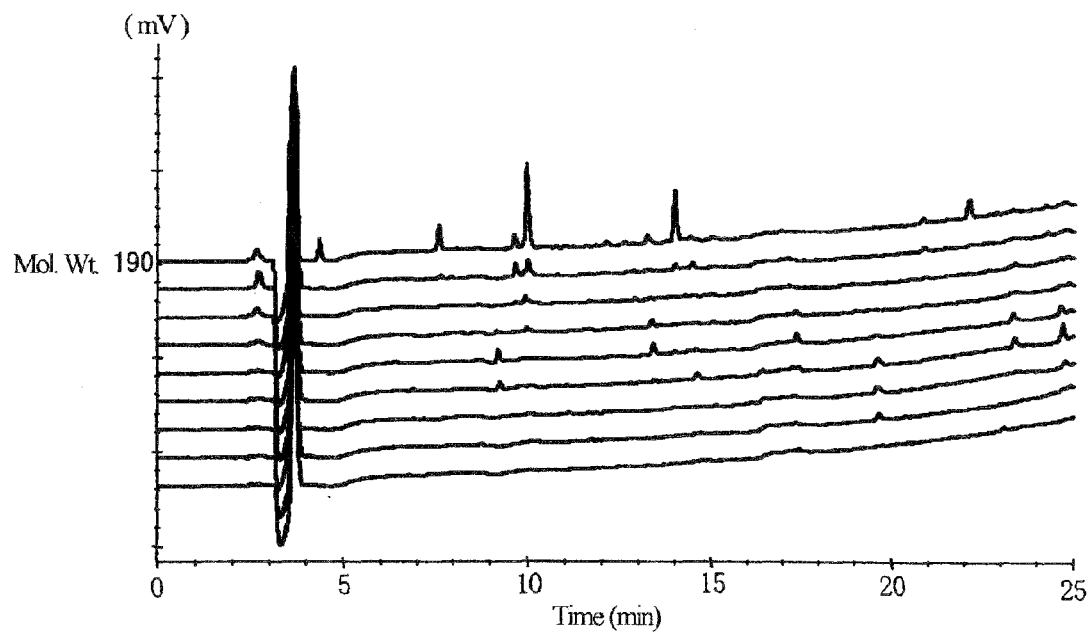

[Fig.10]
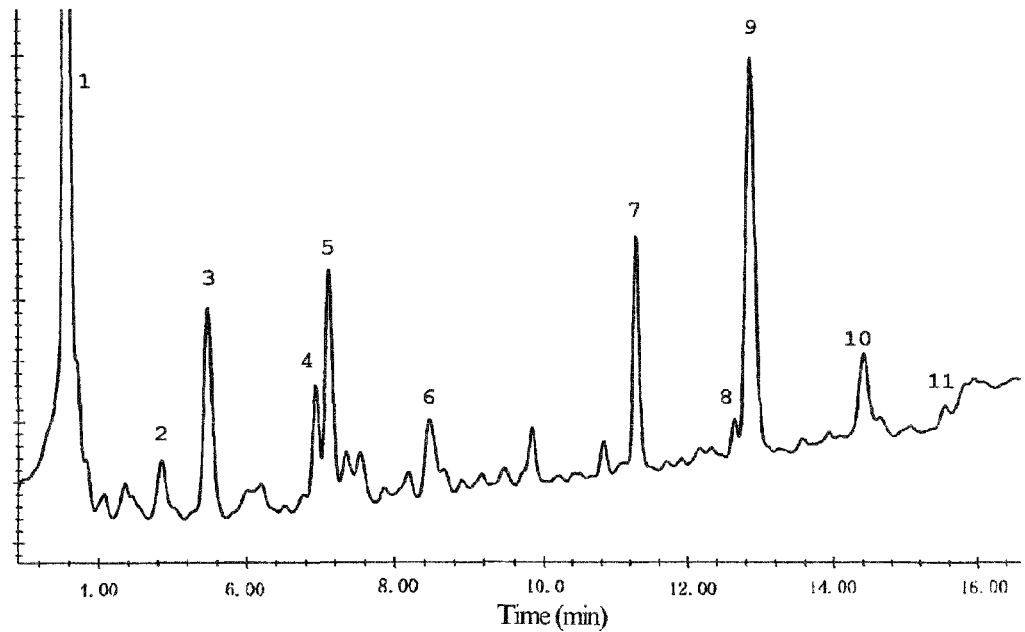
[Fig.11]
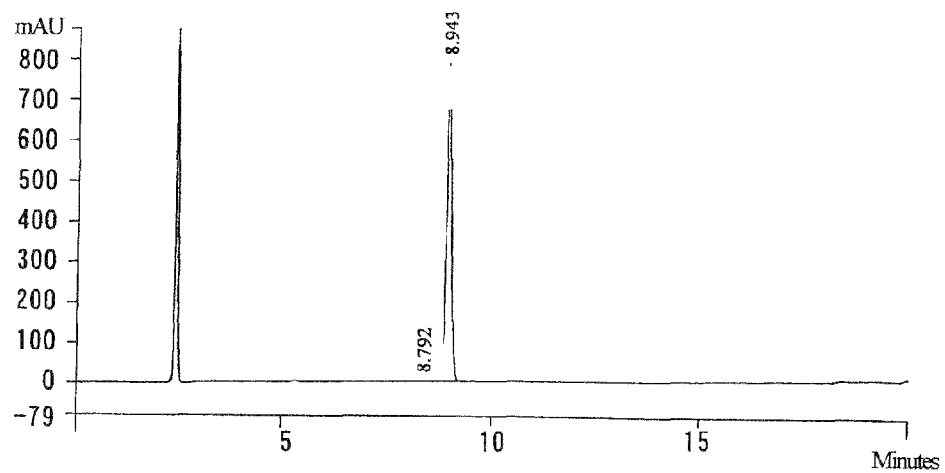

[Fig.12]
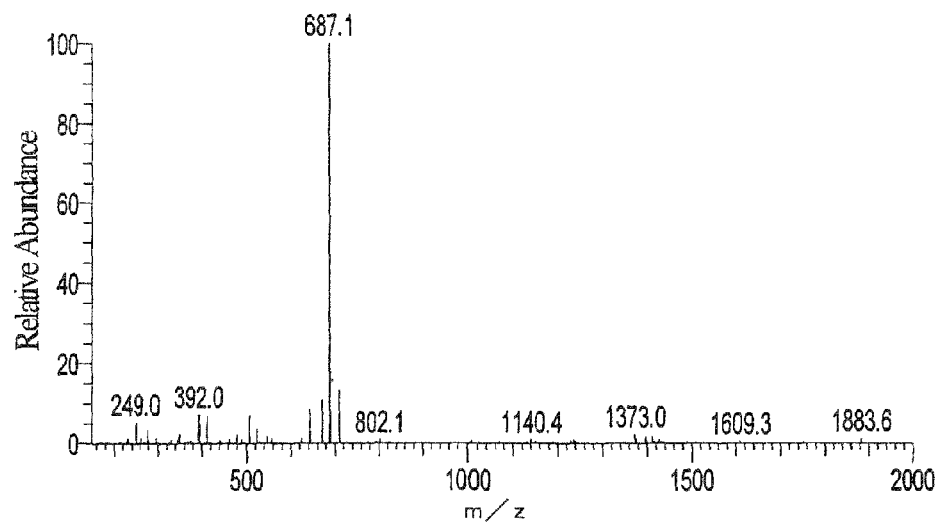
[Fig.13]
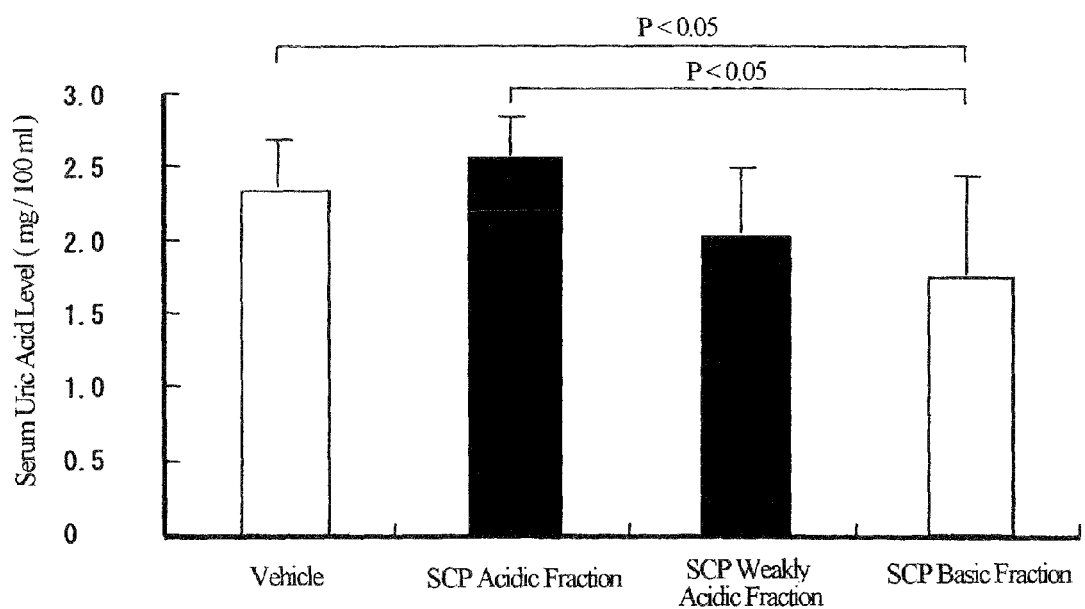

[Fig.14]
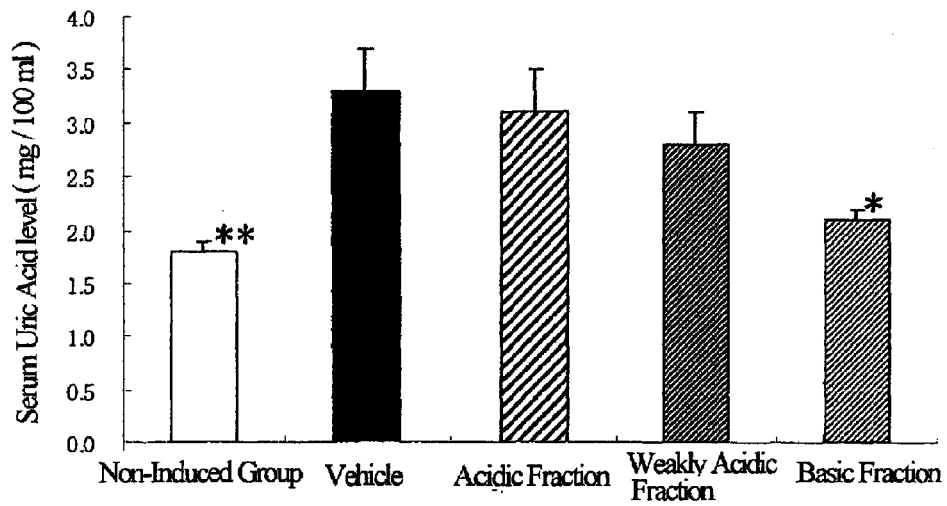
[Fig.15]
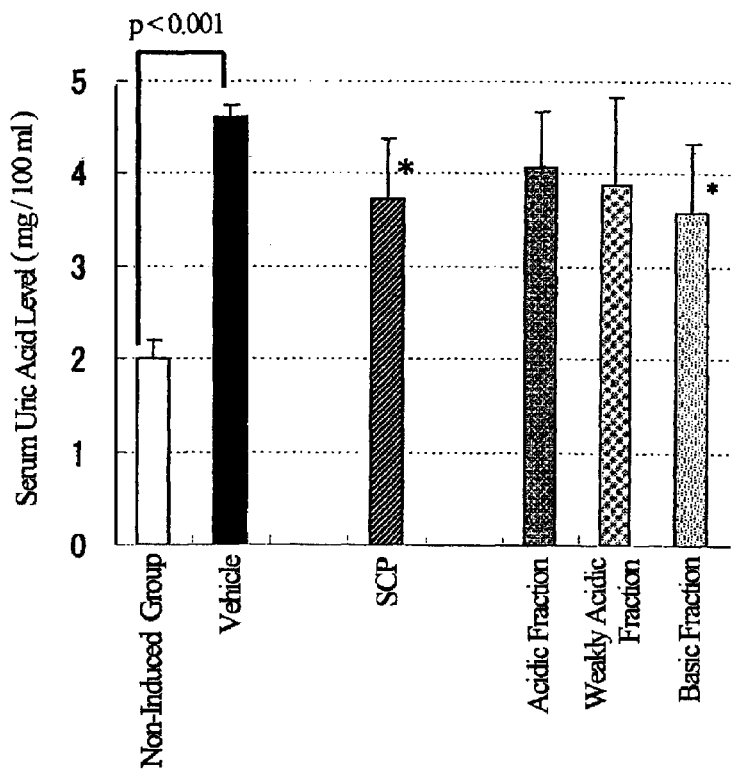

[Fig.16]
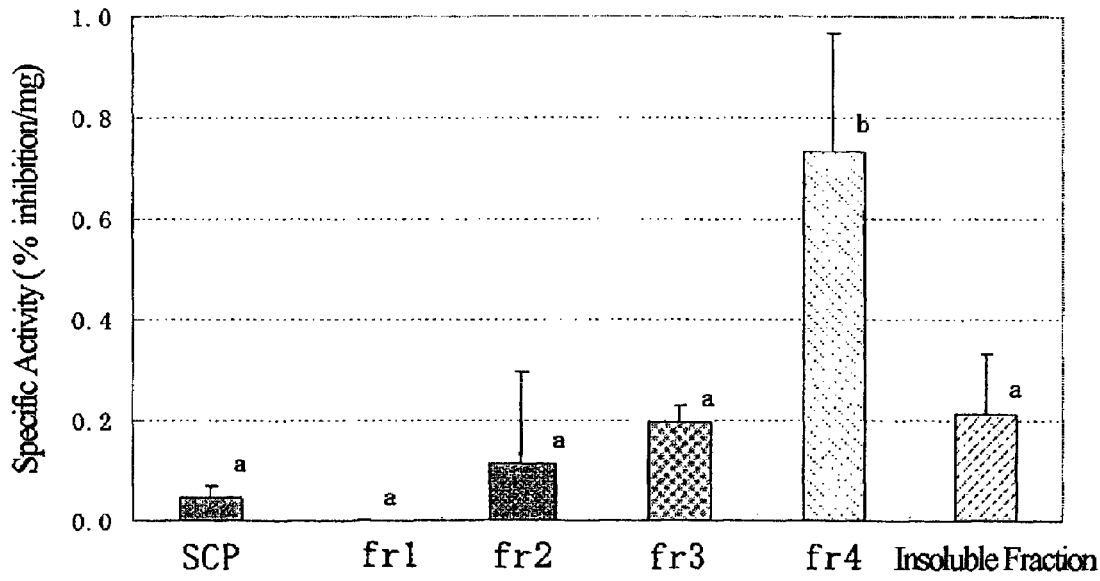
[Fig.17]
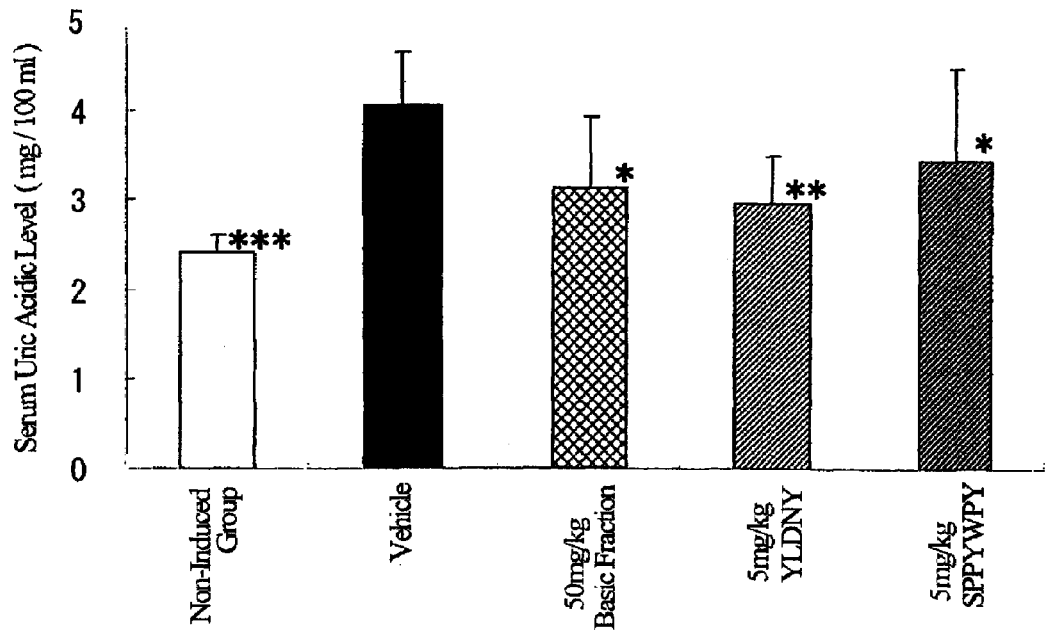

[Fig.18]
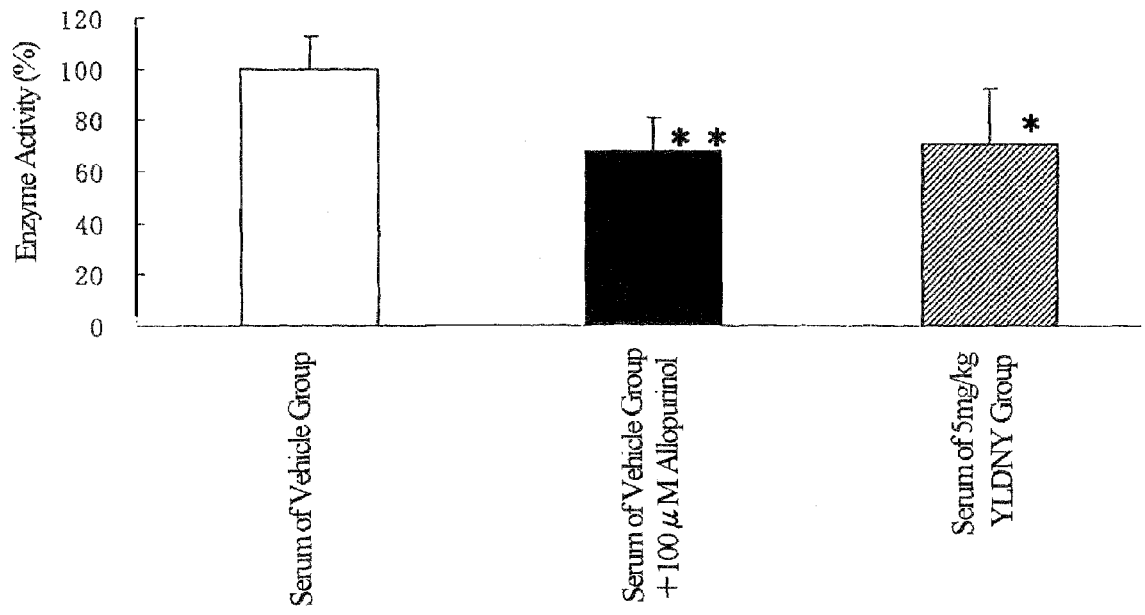
[Fig.19]
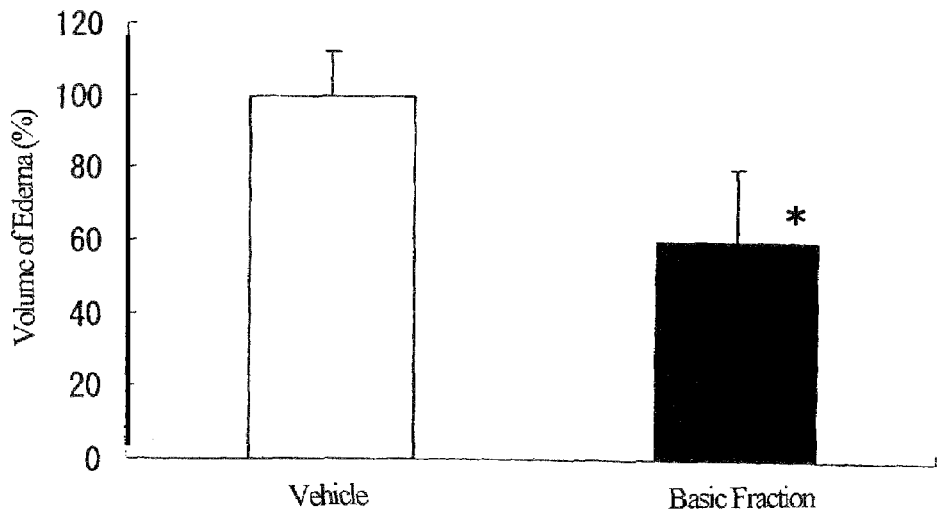

[Fig.20]
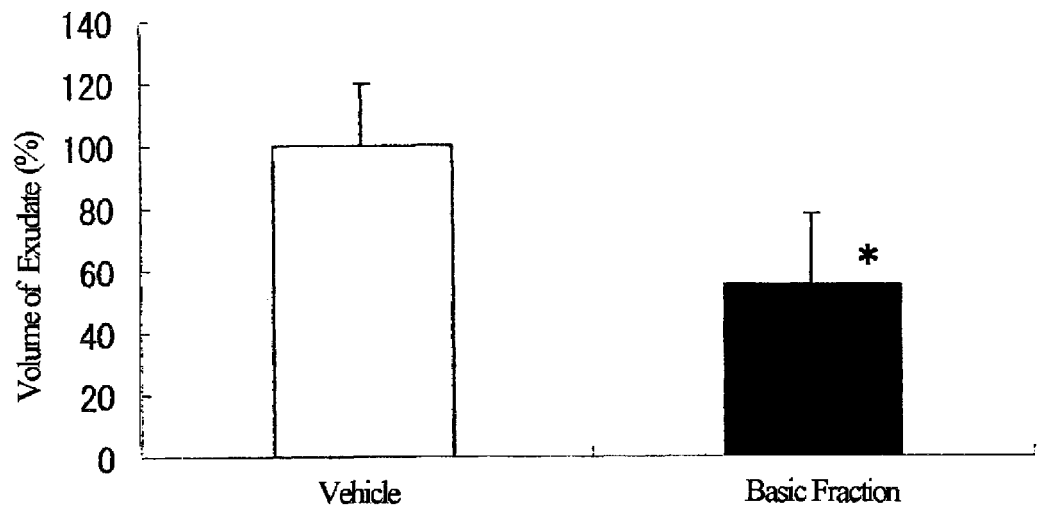
[Fig.21]
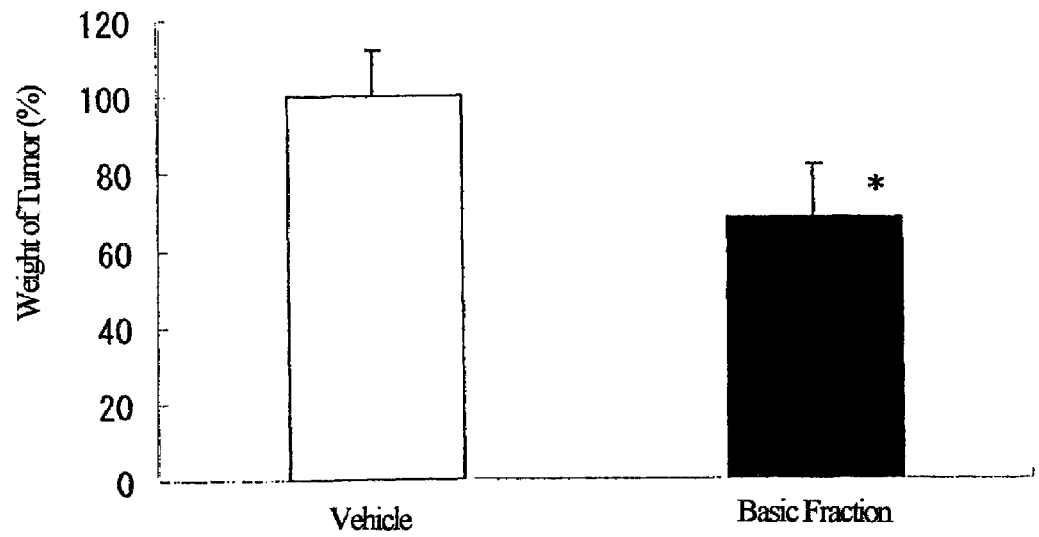

[Fig.22]
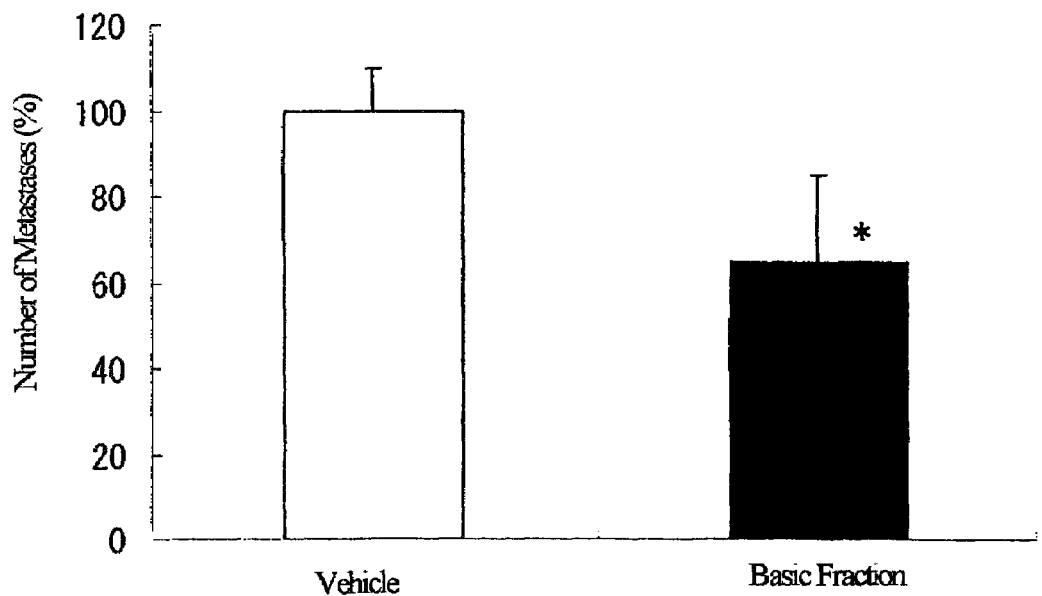
[Fig.23]
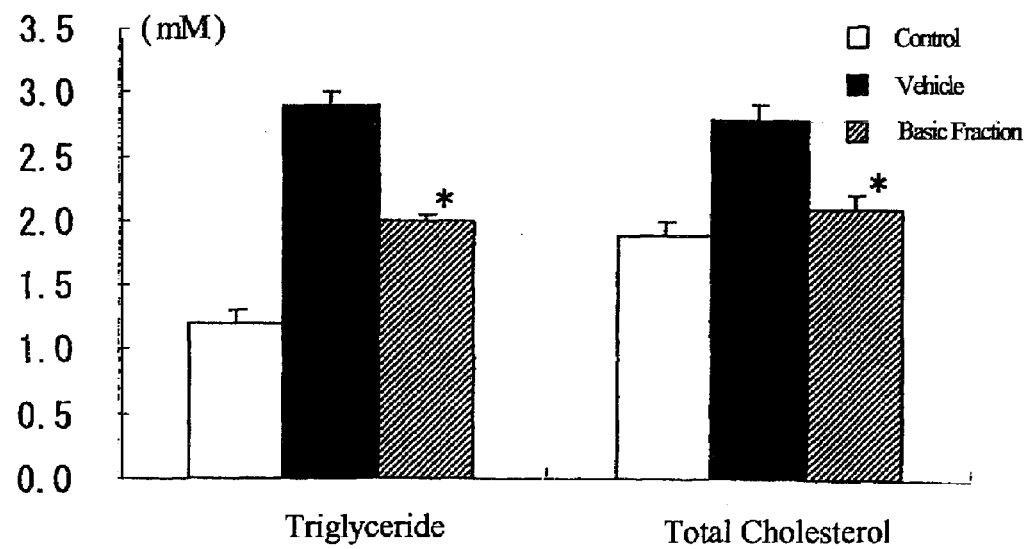

[Fig.24]
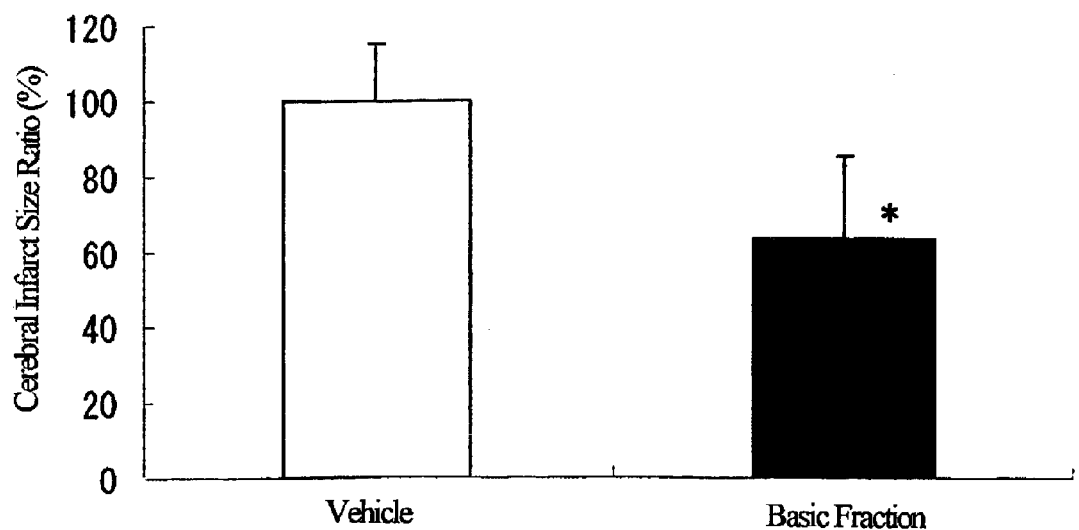
[Fig.25]
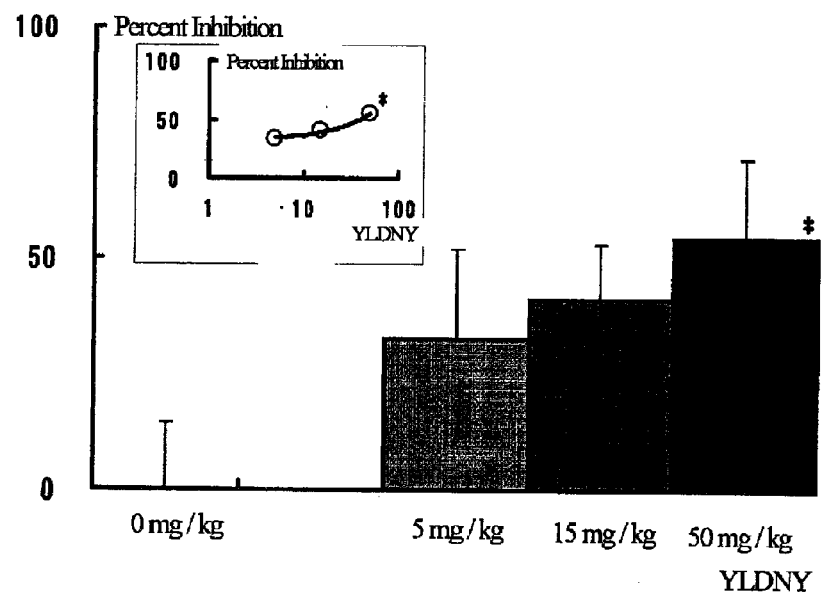

[Fig.26]
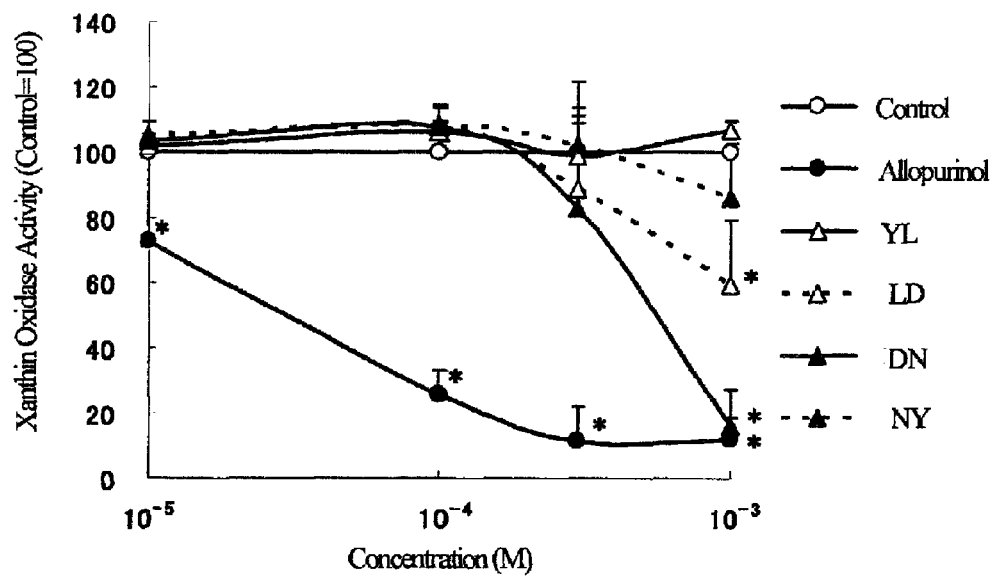
[Fig.27]
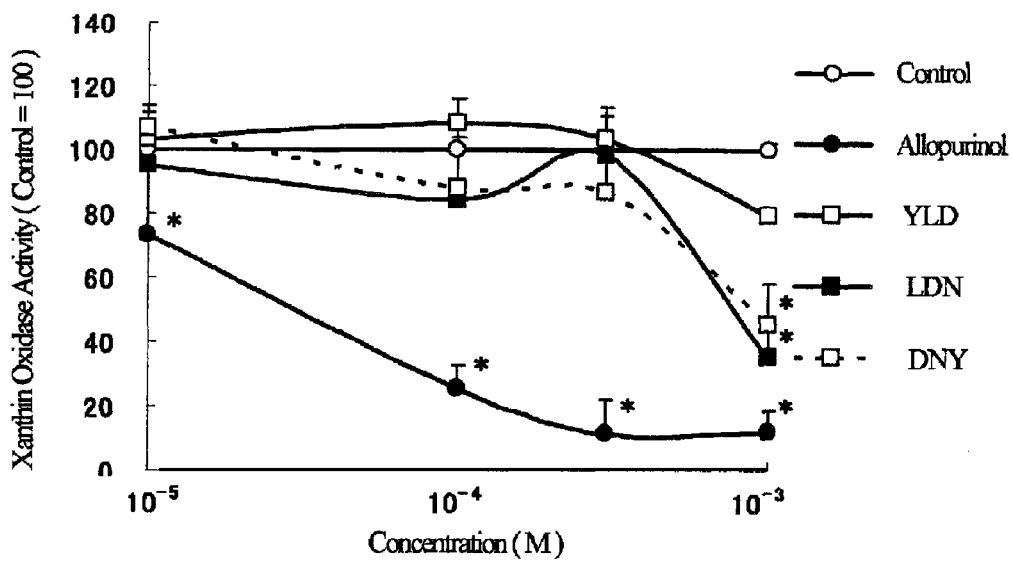

[Fig.28]
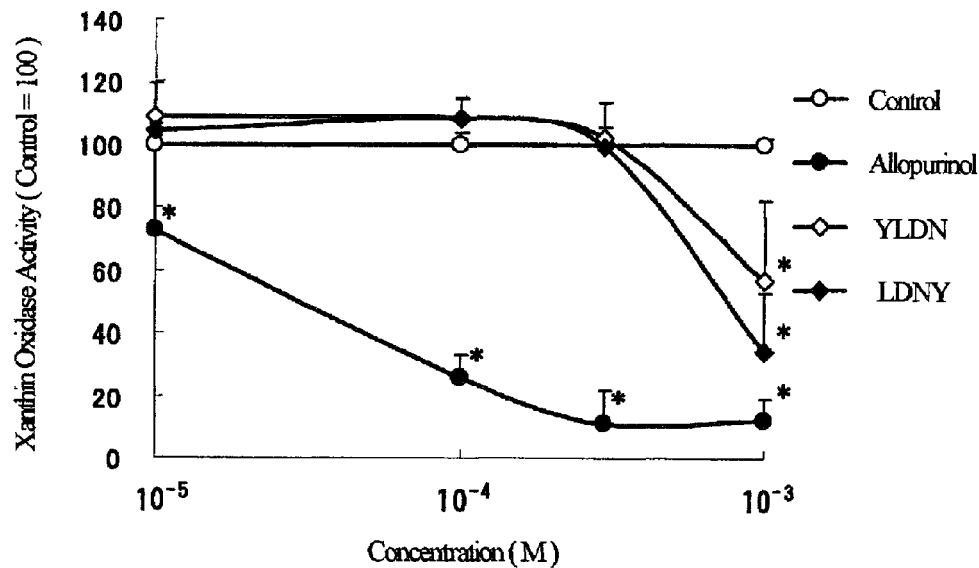
[Fig.29]
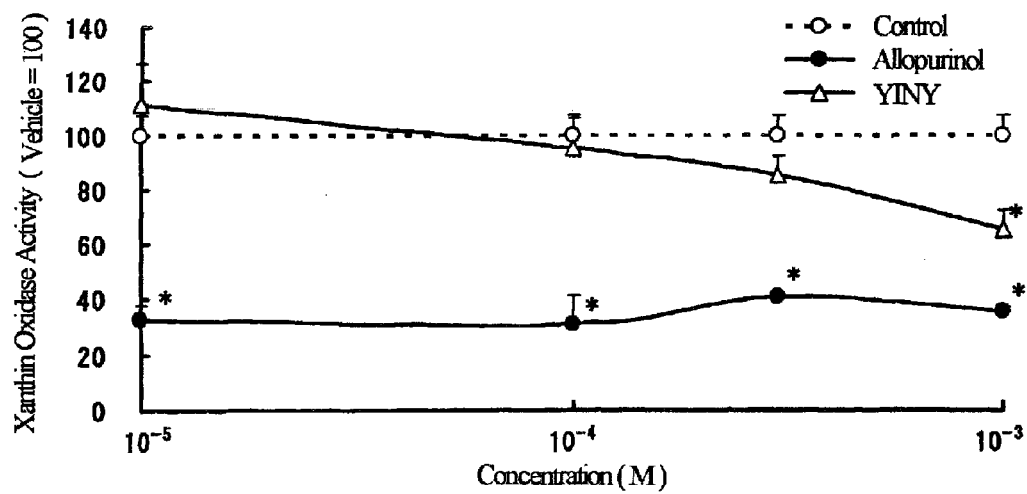

[Fig.30]
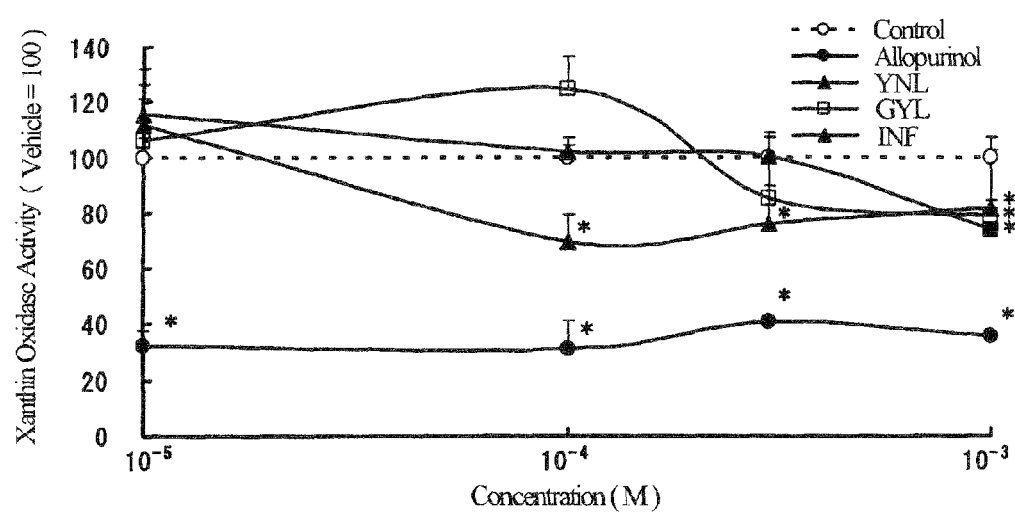

US 7,951,782 B2

COMPOSITION EFFECTIVE TO PREVENT OR TREAT ADULT DISEASE

TECHNICAL FIELD

This invention relates to a composition useful in the fields of foods, beverages, and pharmaceuticals and applicable to the prevention and treatment of adult diseases including hyperuricemia and to a food, a beverage and a pharmaceutical containing the composition. The term "adult disease" as used herein includes cancers and lifestyle-related diseases, including solid cancers, metastatic cancers, gout, hyperuricemia, arteriosclerotic diseases, coronary artery diseases, cerebrovascular disorders, peripheral circulatory disturbances, diabetes, and hypertension.

BACKGROUND ART

Among lifestyle habits, a dietary habit is heavily influential on one's health. An unhealthy diet habit is one of causes of adult diseases or lifestyle-related diseases like cancers, gout, hyperuricemia, hyperlipemia, arteriosclerotic diseases, coronary artery diseases, cerebrovascular disorders, and hypertension. Many of these symptoms are mutually influential on each other. Therefore, not only does a single symptom develop, but two or more symptoms often appear at the same time. For example, major coronary risk factors include hypertension and diabetes (from Japan Atherosclerosis Society (JAS) Guidelines for Prevention of Atherosclerotic Cardiovascular Diseases (2002)). Hypertension and diabetes are also listed as risk factors for hyperlipemia (see Non-Patent Document 1). Cases are also known in which patients with gout suffer a complication such as hypertension or diabetes. In Japan today, nearly two-thirds of causes of death are associated with adult diseases or lifestyle-related diseases. To address this problem, The Ministry of Health, Labor and Welfare, Japan (MHLW) has been promoting the "Healthy Japan 21" campaign since 2000 (from annual reports of MHLW).

While having a balanced diet is ideal, modern people tend to have a disorderly diet, and quite a few people compensate for the imbalance of their diet by taking nutritional supplement. Cartilage of animal origin, such as shark cartilage or bovine cartilage, is one of drug substances or materials of nutritional supplement that have been used over the years. Some of such cartilage extracts with high purity have been employed for medication, and those with relatively low purity in form of a carbohydrate or peptide mixture have been mostly made use of as foodstuffs, either solid or liquid. Animal cartilage is decomposed, extracted, and purified to obtain two types of products in the marketplace. One type is those featuring polysaccharides such as chondroitin sulfate and proteoglycans consisting of core protein and a polysaccharide bound thereto and supplied as hyaluronic acid, chondroitin sulfate or chondroitin sulfate protein complexes. The other type is those featuring protein components derived from collagen and supplied as collagen or collagen peptides. A few examples of these products include chondroitin sulfate for medical use, chondroitin sulfate SCP for edible use, and fish collagen WP (all available from Maruha Corp.). It is said that continued dosing of these products produces beneficial effects in preventing adult diseases such as a cancer and lifestyle-related diseases such as arteriosclerotic diseases and hyperuricemia, reducing joint pains, improving skin conditions, suppressing aging, and the like. For example, continued ingestion of chondroitin sulfate SCP for edible use (from Maruha Corp.) produces beneficial effects in preventing hyperuricemia, gout, and osteoporosis (see Patent Document 1 and Patent Document 2).

Non-Patent Document 1: Nobuhiro Yamada (ed.), Junkanki Now 12, Doumyakukouka Koushiketsusyo, p. 153
Patent Document 1 Japanese Unexamined Patent Application Publication No. 2003-335698
Patent Document 2 Japanese Unexamined Patent Application Publication No. 2003-3248170

DISCLOSURE OF THE INVENTION

While we have knowledge about the physiological actions of chondroitin sulfate or collagen per se, many of active ingredients contained in a composition obtained by purifying an animal cartilage extract remains to be elucidated.

Accordingly, the present invention is contemplated to elucidate the active ingredient present in an animal cartilage extract and to provide a composition containing the active ingredient and effective on the prevention and treatment of adult diseases such as hyperuricemia and a method of using the composition.

As a result of extensive and intensive investigations, the present inventor have found that an enzymatic digestion product of a fraction showing basicity of a cartilage extract has good effect on adult diseases like hyperuricemia. On further fractionating the fraction with basicity using a reverse-phase column, one of the adsorbed fractions exhibited the above mentioned action. This fraction was found to have a molecular weight less than 50,000 Da as a result of GPC analysis and to contain aspartic acid, glutamic acid, proline, glycine, alanine, leucine, tyrosine, lysine, and alginine as a result of amino acid analysis. As a result of pattern analysis by HPLC, an enzymatic digestion product of the fraction was found to comprise 20 or more major polypeptides and their enzymatic digestion products.

The present invention has been completed based on these findings. The invention provides a composition effective to prevent or treat an adult disease which contains as an active ingredient an enzymatic digestion product obtained by enzymatically digesting a basic fraction of an animal cartilage extract.

The invention also provides a polypeptide composition effective to prevent or treat an adult disease which contains as an active ingredient at least one of a polypeptide having an amino acid sequence represented by any one of SEQ ID Nos. 1 to 10, a polypeptide having an amino acid sequence Leu-Tyr, a polypeptide having an amino acid sequence Phe-Tyr, a polypeptide having an amino acid sequence Tyr-Tyr, a polypeptide having an amino acid sequence Ser-Leu, a polypeptide having an amino acid sequence Tyr-Phe, a polypeptide having an amino acid sequence Tyr-Leu, a polypeptide having an amino acid sequence Leu-Phe, a polypeptide having an amino acid sequence Arg-Tyr-Phe, a polypeptide having an amino acid sequence Val-Tyr-Gln, a polypeptide having an amino acid sequence Tyr-Asn-Leu, a polypeptide having an amino acid sequence Gly-Tyr-Leu, a polypeptide having an amino acid sequence Gly-Phe-Leu, a polypeptide having an amino acid sequence Ile-Asn-Phe, a polypeptide having an amino acid sequence Val-Glu-Tyr, a polypeptide having an amino acid sequence Ile-Asn-Tyr, a polypeptide having an amino acid sequence Ile-Tyr-Leu, a part of any of the polypeptides just recited, a polypeptide having in part any of the amino acid sequences recited above, as well as a pharmaceutically acceptable salt of each of the above-recited polypeptides.

The invention also provides a food, beverage or pharmaceutical preparation containing the above-described composition.

BRIEF DESCRIPTION OF THE DRAWINGS

FIG. 1 schematically shows an isoelectric focusing apparatus used in Examples.

FIG. 2 shows the total amino acid concentration, chondroitin sulfate concentration and pH of each cell in fractionating a shark cartilage extract by isoelectric focusing.

FIG. 3 shows the total amino acid concentration, chondroitin sulfate concentration and pH of each cell in fractionating chondroitin sulfate SCP for edible use (from Maruha Corp.) by isoelectric focusing.

FIG. 4 shows a chromatogram of a basic fraction of a shark cartilage extract obtained by reverse-phase column fractionation.

FIG. 5 shows chromatograms (elution patterns) of reverse-phase column fraction fr4 of the basic fraction of a shark cartilage extract before and after alcalase digestion.

FIG. 6 is a chromatogram of GPC analysis on reverse-phase column fraction fr4 of the basic fraction of a shark cartilage extract.

FIG. 7 is a chromatogram of GPC analysis on reverse-phase column fraction fr4 of the basic fraction of a shark cartilage extract.

FIG. 8 is a chromatogram of GPC analysis on alcalase-digested reverse-phase column fraction fr4 of the basic fraction of a shark cartilage extract.

FIG. 9 is a chromatogram of GPC analysis on alcalase-digested reverse-phase column fraction fr4 of the basic fraction of a shark cartilage extract.

FIG. 10 is a chromatogram in fractionating polypeptides contained in alcalase-digested reverse-phase column fraction fr4 of the basic fraction of a shark cartilage extract.

FIG. 11 is an HPLC pattern of a synthetic polypeptide having an amino acid sequence represented by SEQ ID No. 1 (YLDNY).

FIG. 12 is an HPLC-mass chromatogram of a synthetic polypeptide having an amino acid sequence represented by SEQ ID No. 1 (YLDNY).

FIG. 13 is a graph showing the serum uric acid level lowering activity of chondroitin sulfate SCP (for edible use) fractions in normal rats.

FIG. 14 is a graph showing the serum uric acid level lowering activity of an alcalase-digested fraction of a shark cartilage aqueous extract in rat models of hyperuricemia induced by a potassium oxonate-containing diet.

FIG. 15 is a graph showing the serum uric acid level lowering activity of an alcalase-digested fraction of a shark cartilage aqueous extract in rat models of hyperuricemia induced by intraperitoneal administration of potassium oxonate.

FIG. 16 is a graph showing the serum uric acid level lowering activity of alcalase digestion products of reverse-phase column fractions of the basic fraction of a shark cartilage extract.

FIG. 17 is a graph showing the serum uric acid level lowering activity of polypeptides contained in alcalase-digestion products of reverse-phase column fractions of the basic fraction of a shark cartilage extract.

FIG. 18 is a graph showing the inhibitory activity on uric acid synthetase in serum administered with a polypeptide having an amino acid sequence represented by SEQ ID No. 1 (YLDNY).

FIG. 19 is a graph showing the activity of an alcalase-digested basic fraction of a shark cartilage extract on gout in rat paw edema induced by urate.

FIG. 20 is a graph showing the activity of an alcalase-digested basic fraction of a shark cartilage extract on gout in rat air-pouch models induced by uric acid needle-like crystals.

FIG. 21 is a graph showing the activity of an alcalase-digested basic fraction of a shark cartilage extract on a solid cancer.

FIG. 22 is a graph showing the activity of an alcalase-digested basic fraction of a shark cartilage extract on a metastatic cancer.

FIG. 23 is a graph showing the serum triglyceride and total cholesterol levels in mouse models of hyperlipemia given an alcalase-digested basic fraction of a shark cartilage extract over 28 days.

FIG. 24 is a graph showing the cerebral infarct size ratio in rat models of cerebrovascular disorder given an alcalase-digested basic fraction of a shark cartilage extract over 28 days.

FIG. 25 is a graph showing the serum uric acid level lowering activity of a polypeptide having an amino acid sequence represented by SEQ ID No. 1 (YLDNY) in rat models of hyperuricemia induced by intraperitoneal administration of potassium oxonate.

FIG. 26 is a graph showing the uric acid synthetase inhibitory activity of a peptide having a part (number of amino acids: 2) of the sequence of a polypeptide having an amino acid sequence represented by SEQ ID No. 1 (YLDNY).

FIG. 27 is a graph showing the uric acid synthetase inhibitory activity of a peptide having a part (number of amino acids: 3) of the sequence of a polypeptide having an amino acid sequence represented by SEQ ID No. 1 (YLDNY).

FIG. 28 is a graph showing the uric acid synthetase inhibitory activity of a peptide having a part (number of amino acids: 4) of the sequence of a polypeptide having an amino acid sequence represented by SEQ ID No. 1 (YLDNY).

FIG. 29 is a graph showing the uric acid synthetase inhibitory activity of a polypeptide having an amino acid sequence represented by SEQ ID No. 2 (YINY).

FIG. 30 is a graph showing the uric acid synthetase inhibitory activity of polypeptides (YNL, GYL, and INF) contained in an enzymatic digestion product of a reverse-phase column fraction of the basic fraction of a shark cartilage extract.

BEST MODE FOR CARRYING OUT THE INVENTION

The composition according to the present invention, which is effective on the prevention and treatment of adult diseases, will be described with respect to its preferred embodiments.

The composition of the invention is obtained by enzymatically digesting a basic fraction of an animal cartilage extract.

Examples of the animal cartilage used as a raw material of the composition include cartilage of cartilaginous fishes, teleostean fishes, mammals, birds, reptiles, amphibians, crustaceans, and mollusks, preferably cartilage of cartilaginous fishes, teleostean fishes, mammals, birds, and mollusks, more preferably cartilage of cartilaginous fishes, teleostean fishes, and mammals, even more preferably cartilage of cartilaginous fishes and teleostean fishes, most preferably cartilage of cartilaginous fishes.

The animal cartilage extract that can be used in the invention is obtained by extracting the animal cartilage with an appropriate solvent such as water and an alcohol. Animal cartilage of two or more different kinds may be used in combination. In using cartilage of cartilaginous fishes, teleostean fishes and mammals, extraction is preferably preceded by enzymatic treatment.

Commercially available animal cartilage extracts may be used as a cartilage extract, including chondroitin sulfate SCP for edible use (from Maruha Corp.), chondroitin sulfate (food grade) (from Shin Nippon Yakugyo Co., Ltd.), and SNC-20 and SNC-40 (both form Nichiro Corp.), Chondroitin Q (from Q.P. Corp.), Fish Collagen WP (from Maruha Corp.), collagen peptide (enzyme-digested) (from Wako Pure Chemical, Ind., Ltd.), Marine Matrix (from Yaizu Suisankagaku Industry), chicken gelatin (from Nippon Meat Packers, Inc.), and P-LAP (from Nippon Meat Packers, Inc.).

The basic fraction of the animal cartilage extract is obtained by fractionating the extract by, for example, isoelectric focusing.

The basic fraction is preferably a fraction having an isoelectric point of 9 or higher, more preferably a fraction having an isoelectric point of 11 to 13, even more preferably a fraction having an isoelectric point of the recited range and containing aspartic acid, glutamic acid, proline, glycine, alanine, leucine, tyrosine, lysine, and alginine, particularly preferably a fraction having a molecular weight of less than 50,000 Da as well as the above described requirements.

The enzymatic digestion product that is the active ingredient of the composition is obtained by enzymatically digesting the basic fraction. Enzymes that can be used for enzymatic digestion include alcalase and protease. The enzyme treatment is usually, but not necessarily, carried out by allowing a 5% to 15% substrate solution with the pH adjusted to 6 to 8 to react at 40° to 60° C. for 4 to 12 hours.

It is preferred that the enzyme digestion product contain at least one of a polypeptide having an amino acid sequence represented by any one of SEQ ID Nos. 1 to 10, a polypeptide having an amino acid sequence Leu-Tyr, a polypeptide having an amino acid sequence Phe-Tyr, a polypeptide having an amino acid sequence Tyr-Tyr, a polypeptide having an amino acid sequence Ser-Leu, a polypeptide having an amino acid sequence Tyr-Phe, a polypeptide having an amino acid sequence Tyr-Leu, a polypeptide having an amino acid sequence Leu-Phe, a polypeptide having an amino acid sequence Arg-Tyr-Phe, a polypeptide having an amino acid sequence Val-Tyr-Gln, a polypeptide having an amino acid sequence Tyr-Asn-Leu, a polypeptide having an amino acid sequence Gly-Tyr-Leu, a polypeptide having an amino acid sequence Gly-Phe-Leu, a polypeptide having an amino acid sequence Ile-Asn-Phe, a polypeptide having an amino acid sequence Val-Glu-Tyr, a polypeptide having an amino acid sequence Ile-Asn-Tyr, a polypeptide having an amino acid sequence Ile-Tyr-Leu, a part of any of the polypeptides recited, a polypeptide having in part any of the amino acid sequences recited, as well as a pharmaceutically acceptable salt of each of the above-recited polypeptides. It is more preferred that the enzyme digestion product contain at least one of a polypeptide having an amino acid sequence represented by any one of SEQ ID Nos. 1 to 10, a polypeptide having an amino acid sequence Arg-Tyr-Phe, a polypeptide having an amino acid sequence Val-Tyr-Gln, a polypeptide having an amino acid sequence Tyr-Asn-Leu, a polypeptide having an amino acid sequence Gly-Tyr-Leu, a polypeptide having an amino acid sequence Ile-Asn-Tyr, a polypeptide having an amino acid sequence Ile-Tyr-Leu, a polypeptide having an amino acid sequence Tyr-Leu-Asp, a polypeptide having an amino acid sequence Leu-Asp-Asn, a polypeptide having an amino acid sequence Asp-Asn-Tyr, and a pharmaceutically acceptable salt of each of the polypeptides recited.

The composition of the invention may be a polypeptide composition containing at least one of the polypeptides recited above and their salts as an active ingredient. The polypeptide or a salt thereof as an active ingredient of the polypeptide composition may be either one artificially synthesized through an organic synthesis technique or a fermentation technique using a microorganism or one isolated from naturally occurring substances including the above described cartilage of animal origin.

The following is a preferred example of synthesis of the polypeptide or a salt thereof. Animal cartilage is ground to powder and extracted with a sufficient amount of water. The extract is fractionated by, for example, electrofocusing, reverse-phase column chromatography, gel permeation column chromatography, or ultrafiltration to obtain the polypeptide or its salt. The organic synthesis techniques include methods of chemical synthesis such as the commonly employed Fmoc method.

The polypeptides recited as an active ingredient of the composition occur in natural substances that have ingested for generations and pose no safety problem.

The salts of the polypeptides include physiologically acceptable salts with acids (e.g., inorganic and organic acids) or bases (e.g., alkali metal salts). Physiologically acceptable acid addition salts are preferred. Examples of such salts include, but are not limited to, salts with inorganic acids (e.g., hydrochloric acid, phosphoric acid, hydrobromic acid, and sulfuric acid) and organic acids (e.g., acetic acid, formic acid, propionic acid, fumaric acid, maleic acid, tartaric acid, succinic acid, citric acid, malic acid, oxalic acid, benzoic acid, methanesulfonic acid, and benzenesulfonic acid).

The composition can be formulated into dose forms for oral administration, such as tablets, powders, granules, troches, and capsules, together with an appropriate solid carrier such as lactose, terra alba, sucrose, dextrin, talc, gelatin, agar, pectin, acacia, or magnesium stearate; or syrups or soft gelatin capsules together with a liquid carrier such as syrup, vegetable oil or water. The composition may be incorporated into foods, either solid or liquid, to be ingested together.

If desired, the composition may contain an isotonic agent (e.g., sugars or salts), a buffering agent for adjusting to a pH suitable for ingestion, a surface active agent, an antioxidant, an absorption retarder, and so on.

EXAMPLES

The following is Examples for demonstrating the effects of the invention, but it should be understood that the invention is not construed as being limited thereto.

Example 1

Preparation of Animal Cartilage Extract

Shark cartilage powder (250 g) was stirred in 1200 ml of distilled water and centrifuged at 3000 rpm for 10 minutes to collect the supernatant. To the residue was added 200 ml of distilled water, followed by stirring, centrifugation, and collecting the supernatant. The same cycle of operations was repeated once more. The collected supernatant portions were combined and lyophilized using a freeze dryer FD-81 (Tokyo Rikakikai Co., Ltd.) to give a shark cartilage extract weighing 50 g.

Example 2

Preparation of Animal Cartilage Extract

Bovine scapula cartilage (250 g) was heated to dissolve in 1000 ml of distilled water at 120° C. for 120 minutes. After cooling to 50° C., 400 μl of commercially available alcalase was added and allowed to react for 3 hours. After the reaction, 2000 ml of denatured ethanol was added followed by stirring. The supernatant was collected, dried in vacuo to be freed of the denatured alcohol, and lyophilized to give a bovine cartilage extract weighing 62 g.

Example 3

Separation of Basic Fraction from Shark Cartilage Extract

The shark cartilage extract (50 g) obtained in Example 1 was dissolved in water to make a 10% aqueous solution. The solution was fractionated into 10 fractions by taking advantage of difference of isoelectric points of components on a 5 liter electrofocusing apparatus having 10 cells. A voltage of 500 V was applied to the apparatus, and the electrophoresis was ended on confirming that the current passing through the cells became constant. After the fractionation, solutions were collected from the cells having a pH of 9 or higher, combined, and lyophilized (FD-81) to yield a basic fraction. A sketch of the electrofocusing apparatus used is shown in FIG. 1. The isoelectric points of the basic fraction of the shark cartilage extract are shown in Table 1, and the yields of the basic fraction are shown in Table 2. FIG. 2 shows the total amino acid concentration, chondroitin sulfate concentration, and pH of each cell after the fractionation of the shark cartilage extract by electrofocusing. Separately, 50 g of chondroitin sulfate SCP for edible use (Maruha Corp.) was fractionated under the same conditions as above. The total amino acid concentration, chondroitin sulfate concentration, and pH of each cell are shown in FIG. 3. In the electrofocusing apparatus illustrated in FIG. 1, cells 1 to 4 and cells 7 to 10 were filled with distilled water, and every adjacent cells were separated via a semipermeable membrane.

TABLE 1

Isoelectric points of basic fraction of shark cartilage extract

|  | 1$^{st}$ Time | 2$^{nd}$ Time | 3$^{rd}$ Time | 4$^{th}$ Time | 5$^{th}$ Time | 6$^{th}$ Time |
|---|---|---|---|---|---|---|
| Isoelectric Point | 9.6-12.7 | 11.4-12.3 | 11.2-11.4 | 11.0-11.5 | 11.4-11.5 | 11.2-11.3 |

TABLE 2

Yield of basic fraction of shark cartilage extract

|  | 1$^{st}$ Time | 2$^{nd}$ Time | 3$^{rd}$ Time | 4$^{th}$ Time | 5$^{th}$ Time | 6$^{th}$ Time |
|---|---|---|---|---|---|---|
| Amount of Extract per Batch (g) | 10.0 | 10.0 | 7.9 | 7.8 | 10.0 | 9.7 |
| Amount of Basic Fraction Collected (g) | 1.7 | 1.4 | 1.0 | 1.2 | 1.7 | 1.2 |
| Yield (%) | 17.4 | 14.1 | 13.3 | 15.7 | 17.0 | 12.0 |

Example 4

Fractionation of Basic Fraction of Shark Cartilage Extract by Reverse Phase Column Chromatography Two grams of the basic fraction of the shark cartilage extract was further fractionated using a 2 cm×20 cm column packed with Bakerbond C18. The elution rate was 10 ml/min (eluent: water containing 0.1% TFA), and the absorbance of the eluate was monitored at 280 nm. A solution of 2 g of the basic fraction in 100 ml of the eluent was loaded onto the column. The column was washed with a sufficient amount (250 ml) of the eluent to recover a non-adsorbed fraction. The column was then eluted with an acetonitrile gradient from 0% to 60% in 20 minutes. Of the collected effluent inclusive of the eluent used for washing, the fraction from 295 to 350 ml was taken as fr2, the fraction from 350 to 400 ml as fr3, and the fraction from 400 to 500 ml as fr4, respectively.

The fraction insoluble in the eluent was collected separately. All the fractions collected were lyophilized (FD-81). The chromatogram of the reverse phase column fractionation is shown in FIG. 4. The results of the fractionation are shown in Table 3. The amino acid contents of fr4 are shown in Table 4.

TABLE 3

Results of reverse phase column fractionation of basic fraction

| Fraction (fr) No. |  | Weight of Powder (g) | Ratio to Total Basic Fraction (%) | Ratio to Shark Cartilage Extract (%) |
|---|---|---|---|---|
| 1 | non-adsorbed | 7.7 | 92.9 | 14.0 |
| 2 | adsorbed | 0.2 | 1.9 | 0.3 |
| 3 | adsorbed | 0.2 | 2.5 | 0.4 |
| 4 | adsorbed | 0.1 | 0.8 | 0.1 |
| Insoluble fraction | insoluble in eluent | 0.2 | 2.0 | 0.3 |
| Total |  | 8.3 | 100.0 | 15.1 |

TABLE 4

Amino acid contents of reverse phase column fraction fr4 of basic fraction of shark cartilage extract

| Component | Content (μg/mg) |
|---|---|
| Asp | 74.8 |
| Glu | 99.4 |
| Hyp | 29.7 |

TABLE 4-continued

Amino acid contents of reverse phase column fraction fr4 of basic fraction of shark cartilage extract

| Component | Content (µg/mg) |
|---|---|
| Ser | 37.7 |
| Gly | 61.2 |
| His | 12.1 |
| Arg | 48.2 |
| Thr | 27.3 |
| Ala | 37.1 |
| Pro | 67.4 |
| Tyr | 27.9 |
| Val | 27.2 |
| Met | 17.3 |
| Ile | 25.9 |
| Leu | 58.4 |
| Hyl1 | 4.8 |
| Hyl2 | 2.3 |
| Phe | 26.8 |
| Lys | 57.1 |
| Total | 742.4 |

Example 5

Confirmation of Elution Patterns of Reverse Phase Column Fraction Fr4 of Basic Fraction of Shark Cartilage Extract and its Alcalase Digestion Product The elution patterns of fr4, one of the reverse phase column fractions of the basic fraction of the shark cartilage extract, and its alcalase digestion product were confirmed under the following conditions. The resulting chromatograms are shown in FIG. 5.
Column: Cosmosil 5C18-MS-II, Nacalai Tesque, Inc. (4.6×250 mm)
Column temperature: 40° C.
Detection wavelength: 230 nm
Analysis time: 40 mins.
Mobile phase: (i) 10% AcCN in water with 0.1% TFA to 80% AcCN in water with 0.1% TFA for 30 mins; (ii) 80% AcCN in water with 0.1% TFA for 30 to 35 mins.
Flow rate: 0.7 ml/min Example 6

GPC Analysis on Reverse Phase Column Fraction Fr4 of Basic Fraction of Shark Cartilage Extract and its Alcalase Digestion Product, and Confirmation of Amino Acid Sequence Of Main Peptides Five milligrams of fr4 or its alcalase digestion product was stirred in 500 µl of distilled water and centrifuged at 12000 rpm for 2 minutes to collect the supernatant. To the residue was added 200 µl of 30% acetonitrile in water with 0.1% TFA, followed by stirring, centrifugation, and collecting the supernatant. The supernatants were combined and lyophilized (FD-81). An aliquot of the resulting sample was loaded on a gel permeation column, and one-minute fractions were collected under the following conditions. Each fraction was concentrated to dryness, re-dissolved in 100 µl of distilled water and analyzed by HPLC under the following conditions. As a result, fr4 was considered to be made up of components having molecular weights less than 50,000. The chromatograms of fr4 are shown in FIGS. 6 and 7, and those of the alcalase-digested fr4 are shown in FIGS. 8 and 9. The alcalase-digested fr4 was further analyzed on an amino acid sequencer (PPSQ-21, Shimadzu Corp.) to confirm the amino acid sequences of the peaks. The results obtained are shown in FIG. 10 and Table 5.
Conditions of Gel Permeation Chromatography:
Packing: Superdex Peptide
Detection wavelength: 230 nm
Analysis time: 40 min
   Mobile phase: 30% AcCN in water, containing 0.1% TFA
   Flow rate: 0.5 ml/min
Conditions of HPLC of fractions:
   Column: Cosmosil 5C18-MS-II, Nacalai Tesque (4.6×250 mm)
   Column temperature: 40° C.
   Detection wavelength: 230 nm
   Analysis time: 40 min
   Mobile phase: (i) 10% AcCN in water with 0.1% TFA to 80% AcCN in water with 0.1% TFA for 30 mins; (ii) 80% AcCN in water with 0.1% TFA for 30 to 35 mins.
   Flow rate: 0.1 ml/min

TABLE 5

| Number | Results of Sequence Determination | | | | | | | | |
|---|---|---|---|---|---|---|---|---|---|
| 2 | Tyr | Ser | Leu | | Tyr | Phe | Try | Leu > Ala > Thr | — |
|   | Tyr | Leu | Tyr | | Phe | Tyr | Leu | Phe > Tyr | |
| 3 | Arg | Val | Tyr | Ile | Val | Gly | Gly > Tyr | Ile > Ser | Ile > Ser > Val |
|   | Tyr | Tyr | Asn | Asn | Glu | Tyr | Phe/Tyr | Asn > Tyr | Tyr > Phe > Asn |
|   | Phe | Gln | Leu | Tyr | Tyr | Leu | Leu | Phe | Leu |
| 4 | Ser | Ser | Val > Ser > Trp | Tyr > Leu | Tyr | Leu | — | — | |
|   | Asn | Ile | Glu | Ile > Ala > Val | Leu | Asp | | | |
|   | Trp | Tyr | Tyr | Asn | Asp | Asn | | | |
|   | Gln | Asp | Phe | Tyr | Asn | Tyr | | | |
| 5 | Asp | Try | — | — | — | — | — | — | |
|   | Phe | Leu | | | | | | | |
|   | Trp | Asp | | | | | | | |
|   | Arg | Asn | | | | | | | |
|   | Tyr | Tyr | | | | | | | |
| 7 | Ser | Ser | — | — | — | — | — | — | |
|   | Leu | Pro | | | | | | | |
|   | Pro | Pro | | | | | | | |
|   | Tyr | Tyr | | | | | | | |
|   | Trp | Trp | | | | | | | |
|   | Pro | Pro | | | | | | | |
|   | Tyr | Tyr | | | | | | | |

Example 7

Synthesis of Polypeptide Having SEQ ID No. 1

The polypeptide having an amino acid sequence shown in SEQ ID No. 1, which is one of the polypeptides contained in the alcalase digestion product of fr4, was synthesized by the Fmoc method. Fmoc-protected amino acids were successively linked by using previously activated corresponding α-amino acid derivatives and a condensing agent. The Fmoc group was removed by treatment with piperidine. The synthesized polypeptide was confirmed by HPLC and HPLC-mass chromatography under the following conditions. The results of the analyses are shown in FIGS. 11 and 12.

Conditions of HPLC:
  Apparatus: Waters 2690
  Column: Discovery, C18 (4.6×250 mm)
  Detection wavelength: 215 nm
  Analysis time: 20 min
  Mobile phase: 0.1% TFA in water to 30% AcCN in water with 0.1% TFA for 20 min
  Flow rate: 1.5 ml/min Conditions of HPLC-Mass Chromatography:
  Apparatus: Agilent 1100 system connected to Thermo Finnigan LCQ Advantage
  Column: Discovery, C18 (4.6×250 mm)
  Analysis time: 0.95 min
  Mobile phase: 0.1% TFA, AcCN (with 0.1% TFA)
  Flow rate: 1.0 ml/min

Example 8

Evaluation on Serum Uric Acid Level Lowering Activity of Chondroitin Sulfate SCP Fraction for Edible Use (Maruha) in Normal Rats Chondroitin sulfate SCP for edible use (Maruha) as a shark cartilage extract was fractionated into an acidic fraction, a weakly acidic fraction, and a basic fraction (38%/25%/37%) by isoelectric focusing in the same manner as in Example 3. One gram/kg B.W./day of each of the fractions (acidic fraction: 1×0.38=380 mg; weakly acidic fraction: 1×0.25=250 mg; basic fraction: 1×0.37=370 mg) was forcibly administered per os to tame, 7-week-old SD male rats through a probe for consecutive 22 days. The rats were fed ad lib. on a diet CRF-1 (from Oriental Yeast Co., Ltd.) and tap water (in Tsukuba City). After the administration period, total blood was collected from the abdominal aorta under anesthesia with Nembutal and evaluated for serum uric acid level using a commercially available kit (Uric Acid B-Test, from Wako Pure Chemical Ind., Ltd.). As a result, the basic fraction of the chondroitin sulfate SCP for edible use was observed to have serum uric acid lowering activity. The results are shown in FIG. 13 (n=6, mean±SD, *P<0.05 vs. vehicle (ANOVA followed by Scheffe test).

Example 9

Evaluation of Serum Uric Acid Level Lowering Activity of Enzyme-Digested Fraction of Shark Cartilage Aqueous Extract in Rat Models of Hyperuricemia Induced by Potassium Oxonate-Containing Diet A shark cartilage aqueous extract prepared in the same manner as in Example 1 was fractionated into an acidic, a weakly acidic, and a basic fraction (66%/24%/10%) by isoelectric focusing, each of which was digested with alcalase. One gram/kg B.W./day of each of the alcalase-digested fractions (acidic fraction: 1×0.66=660 mg; weakly acidic fraction: 1×0.24=240 mg; basic fraction: 1×0.10=100 mg) was forcibly administered per os to tame 7-week-old, SD male rats through a probe for consecutive 28 days. The rats were fed ad lib. on a standard feed containing 2.5% potassium oxonate (i.e., a hyperuricemia inducing diet) and tap water (in Tsukuba City). The composition of the hyperuricemia inducing diet is shown in Table 6. After the administration period, total blood was collected from the abdominal aorta under anesthesia with Nembutal and evaluated for serum uric acid level using a commercially available kit (Uric Acid Test, from Wako Pure Chemical Ind., Ltd.). As a result, the basic fraction of the shark cartilage extract was observed to have serum uric acid lowering activity. The results are shown in FIG. 14 (n=6, mean±SD, **p<0.01, *p<0.05 vs. vehicle (ANOVA followed by Dunnett's test).

TABLE 6

| Composition of hyperuricemia inducing diet | |
|---|---|
| Ingredient | Amount (wt %) |
| Corn starch | 38.0 |
| Casein | 25.0 |
| Alpha-corn starch | 10.0 |
| Cellulose powder | 8.0 |
| Soybean oil | 6.0 |
| Oriental Mineral Mix | 6.0 |
| Oriental Vitamin Mix | 2.0 |
| Sucrose | 2.5 |
| Potassium oxonate | 2.5 |
| Total | 100.0 |

Example 10

Evaluation of Serum Uric Acid Level Lowering Activity of Enzyme-Digested Fraction of Shark Cartilage Aqueous Extract in Rat Models of Hyperuricemia Induced by Intraperitoneal Administration of Potassium Oxonate A shark cartilage aqueous extract prepared in the same manner as in Example 1 was fractionated into an acidic, a weakly acidic, and a basic fraction (66%/24%/10%) by isoelectric focusing, each of which was digested with alcalase. One gram/kg B.W./day of each of the alcalase-digested fractions (acidic fraction: 1×0.66=660 mg; weakly acidic fraction: 1×0.24=240 mg; basic fraction: 1×0.10=100 mg) was forcibly administered per os to tame Wistar male rats weighing 150 to 220 g through a probe. One hour later, a single dose of 250 mg/kg B.W. of potassium oxonate/3% gum arabic saline solution as a hyperuricemia inducing agent was intraperitoneally administered. After 1 hour from the administration of the hyperuricemia inducing agent, blood was collected from the abdominal aorta under anesthesia with Nembutal. The serum separated from the blood sample in a usual manner was evaluated for uric acid level using a commercially available kit (Uric Acid Test, from Wako Pure Chemical). As a result, serum uric acid lowering activity was observed in the basic fraction of the shark cartilage aqueous extract. The results are shown in FIG. 15 (n=6, mean±SD, *p<0.05 vs. vehicle (t-test).

Example 11

Evaluation of Serum Uric Acid Level Lowering Activity of Enzyme-Digested Reverse Phase Column Fraction of Basic Fraction of Shark Cartilage Extract Reverse phase column fractions of a basic fraction of a shark cartilage extract were prepared in the same manner as in Example 4 and digested with alcalase. Each of the enzyme-digested fractions was forcibly administered per os to tame Wistar male rats weighing 150 to 220 g through a probe at a dose decided based on the compositional ratio of the fractions so that the dosage of fr4 that was present in the lowest proportion might be 50 mg/kg B.W. (see Table 7). One hour later, a single dose of 250 mg/kg B.W. of potassium oxonate/3% gum arabic saline solution as a hyperuricemia inducing agent was intraperitoneally administered. After 1 hour from the administration of the hyperuricemia inducing agent, blood was collected from the abdominal aorta under anesthesia with Nembutal. The serum separated from the blood sample in a usual manner was evaluated for uric acid level using a commercially available kit (Uric Acid Test, from Wako Pure Chemical). As a result, serum uric acid lowering activity was observed in the alcalase-digestion product of fr4, one of the fractions adsorbed on the reverse phase column. The results of the evaluation are shown in FIG. 16 (n=6, mean±SD, a, b (significant difference therebetween) $p<0.05$ vs. vehicle (ANOVA followed by Scheffe test). The "specific activity" is expressed in terms of relative percent inhibition per mg of the administered preparation, with the average serum uric acid level of the non-induced group being taking as 0, and that of the vehicle group as 100.

TABLE 7

Dosage of alcalase-digested, reverse-phase column fractions of basic fraction of shark cartilage extract in rat

| | | Ratio to Basic Fraction (%) | Dosage (mg/kg B.W.) |
|---|---|---|---|
| fr1 | non-adsorbed | 92.9 | 5796 |
| fr2 | adsorbed | 1.9 | 119 |
| fr3 | adsorbed | 2.5 | 153 |
| fr4 | adsorbed | 0.8 | 50 |
| Insoluble Fraction | insoluble in eluent | 2.0 | 123 |

Example 12

Evaluation of Serum Uric Acid Level Lowering Activity of Polypeptides Contained in Enzyme-Digested Reverse Phase Column Fraction of Basic Fraction of Shark Cartilage Extract A polypeptide having an amino acid sequence represented by SEQ ID No. 1 (YLDNY) and a polypeptide having an amino acid sequence represented by SEQ ID No. 3 (SPPYWPY), which are contained in the alcalase digestion product of the reverse phase column fraction of the basic fraction, were synthesized by, for example, the process described in Example 7 and each administered to the tail vein of rats at a dose of 5 mg/kg B.W. Immediately thereafter, a single dose of 250 mg/kg B.W. of potassium oxonate/3% gum arabic saline solution as a hyperuricemia inducing agent was intraperitoneally administered. After 1 hour from the administration of the hyperuricemia inducing agent, blood was collected from the abdominal aorta under anesthesia with Nembutal. The serum separated from the blood sample in a usual manner was assayed for serum uric acid level using a commercially available kit (Uric Acid Test, from Wako Pure Chemical). As a result, serum uric acid lowering activity was observed in both the polypeptide having SEQ ID No. 1 (YLDNY) and the polypeptide having SEQ ID No. 3 (SPPYWPY). The results of the evaluation are shown in FIG. 17 (n=8, mean±SD, $*p<0.05$, $p<0.01$, $*p<0.001$ vs. vehicle (t-test).

Example 13

Evaluation of Uric Acid Synthetase Inhibitory Activity of Serum of Rat Administered with Polypeptide Having SEQ ID No. 1

The polypeptide having SEQ ID No. 1 (YLDNY) contained in the alcalase-digested, reverse-phase column fraction of the basic fraction was administered to the tail vein of rats at a dose of 5 mg/kg B.W. One hour later, blood was collected, and serum was separated therefrom. A hundred microliter of the serum was added to 2 ml of a 50 mM tris-HCl buffer (pH 7.4) containing 15 µM xanthine as an enzyme substrate to prepare a reaction system. To the reaction system was added 0.1 unit (containing 100 µl of 25 units/25 ml enzyme solution) of xanthine oxidase (XO) of cow's milk (from Wako Pure Chemical), followed by allowing the system to react at 37° C. for 11 minutes. The amount of uric acid produced from xanthine by the action of xanthine oxidase was assayed in terms of changes in optical density (OD, at 292 nm), from which the enzyme activity was calculated from formula below. As a result, xanthine oxidase activity was inhibited in the system containing the serum of the rat administered with the polypeptide having SEQ ID No. 1 (YLDNY). The results obtained are shown in FIG. 18 (n=6, mean±SD, $**p<0.01$, $*p<0.05$ vs. vehicle (t-test)). Allopurinol was used as dissolved in the reaction system.

Enzyme activity (%)=(increase of OD by addition of XO in reaction system containing serum from each animal)×100/(average increase of OD by addition of XO in reaction system containing serum from vehicle group)

Example 14

Evaluation of Activity of Alcalase-Digested Basic Fraction of Shark Cartilage Extract on Gout in Rat Paw Edema Induced by Urate A basic fraction of a shark cartilage extract prepared in the same manner as in Example 3 was digested with alcalase, and the alcalase-digested fraction was forcibly administered per os to tame Wistar male rats weighing 200 to 250 g at a dose of 100 mg/kg B.W. In a vehicle group, water for injection (from Otsuka Pharmaceutical Co., Ltd.) was administered. Thereafter, 0.1 ml of a 10% solution of uric acid needle-like crystals in saline was subcutaneously administered to the bottom of the left hind paw of the rat under ether anesthesia, and the same dose of saline was subcutaneously administered to the bottom of the right hind paw. The differences between the hind paws in volume of edema developed thereafter were compared between the two groups. As a result, the group administered with the alcalase-digested basic fraction of the shark cartilage extract showed a significantly smaller difference than the vehicle group. The results obtained are shown in FIG. 19 (n=6, mean±SD, $*p<0.05$ vs. vehicle (t-test)). The average of the differences between the hind paws in volume of edema in the vehicle group was taken as 100.

Example 15

Evaluation of Activity of Alcalase-Digested Basic Fraction of Shark Cartilage Extract on Gout in Rat Air-Pouch Models Induced by Uric Acid Needle-Like Crystals A basic fraction of a shark cartilage extract prepared in the same manner as in Example 3 was digested with alcalase, and the alcalase-digested fraction was forcibly orally administered to tame SD male rats weighing 150 to 200 g at a dose of 100 mg/kg B.W./day for consecutive 6 days. In a vehicle group, water for injection (from Otsuka Pharmaceutical Co., Ltd.) was administered. The rats under ether anesthesia were injected subcutaneously with 8 ml of air on the dorsal surface to make an air-pouch, followed 24 hours later by forcible oral administration of the same alcalase-digested basic fraction of the shark cartilage extract at a dose of 100 mg/kg B.W. (water for injection from Otsuka in the vehicle group). Into the air pouch was then injected 4 ml of a 5% solution of uric acid needle-like crystals in a 0.5% carboxymethyl cellulose solution (containing 0.5% casein). After four days from the administration of the uric acid needle-like crystals, the air pouch exudate was collected, measured, and compared with that from the vehicle group. As a result, the group treated with the alcalase-digested basic fraction of the shark cartilage extract showed a significantly smaller volume than the vehicle group. The results obtained are shown in FIG. 20 (n=6, mean±SD, *p<0.05 vs. vehicle (t-test)). The average of the volumes of the exudates in the vehicle group was taken as 100.

Example 16

Evaluation of Activity of Alcalase-Digested Basic Fraction of Shark Cartilage Extract on Solid Cancer The melanoma cell line B16F10 (mouse cancer cells) was implanted into the dorsal region of BDF1 mice. An alcalase digestion product of a basic fraction of a shark cartilage extract prepared in the same manner as in Example 3 (water for injection in the vehicle group) was then intraperitoneally injected at a dose of 300 mg/kg B.W./day for consecutive 14 days. On the 15th day from the start of intraperitoneal injection, the tumor implanted was excised and weighed to evaluate the influences of the administered preparation on the growth of the tumor. As a result, the group treated with the alcalase-digested basic fraction of the shark cartilage extract showed a significantly lower tumor weight than the vehicle group given with distilled water. The results obtained are shown in FIG. 21 (n=9, mean±SD, *p<0.05 vs. vehicle (t-test)). The average of the weights of the tumors in the vehicle group was taken as 100.

Example 17

Evaluation of Activity of Alcalase-Digested Basic Fraction of Shark Cartilage Extract on Metastatic Cancer An alcalase digestion product of a basic fraction of a shark cartilage extract prepared in the same manner as in Example 3 was forcibly orally given to C57BL/6 mice at a dose of 300 mg/kg B.W./day for consecutive 28 days. On the 14th day from the start of the oral administration, the melanoma cell line B16F10 of mouse origin was implanted to the tail vein of the mice. After 28 days from the start of oral administration, the degree of metastasis to the lungs was examined. As a result, the number of lung metastases (black spots) in the group given the alcalase-digested basic fraction of the shark cartilage extract was significantly smaller than in the vehicle group given distilled water. The results obtained are shown in FIG. 22 (n=12, mean±SD, *p<0.05 vs. vehicle (t-test)). The average of the numbers of the metastases in the vehicle group was taken as 100.

Example 18

Evaluation of Activity of Alcalase-Digested Basic Fraction of Shark Cartilage Extract on Arteriosclerosis Mouse models of hyperlipemia created by feeding 4-week-old ICR male mice on a high fat diet containing 40% beef tallow ad lib. were forcibly orally given 100 mg/kg B.W./day of an alcalase digestion product of a basic fraction of a shark cartilage extract prepared in the same manner as in Example 3 for consecutive 28 days. After the administration period, total blood was collected from the abdominal aorta under anesthesia with Nembutal, and serum was obtained therefrom immediately in a usual manner. As a result of measuring triglyceride and total cholesterol levels in the serum, the group administered with the alcalase-digested basic fraction of the shark cartilage extract had significantly lower levels than the vehicle group given distilled water. The composition of the high fat diet used to induce hyperlipemia is shown in Table 8. The results of the serum triglyceride and total cholesterol level measurements are shown in FIG. 23 (n=6, mean±SD, *p<0.05 vs. vehicle (t-test)).

TABLE 8

| Composition of high fat diet | |
|---|---|
| Ingredient | Amount (wt %) |
| Beef tallow | 40.0 |
| Corn starch | 10.0 |
| Glucose | 9.0 |
| AIN-76TM Mineral Mix | 4.0 |
| AIN-76TM Vitamin Mix | 1.0 |
| Casein | 36.0 |
| Total | 100.0 |

Example 19

Evaluation of Cerebrovascular Disorder Inhibitory Activity of Alcalase-Digested Basic Fraction of Shark Cartilage Extract Four-week-old rat models of cerebrovascular disorder induced by middle cerebral artery ligation were forcibly given per os 100 mg/kg B.W./day of an alcalase digestion product of a basic fraction of a shark cartilage extract prepared in the same manner as in Example 3 for consecutive 28 days. As a result, the cerebral infarct size ratio significantly reduced as compared with the vehicle group given distilled water. The cerebral infarct size ratio on the 28th day of administration in comparison with the vehicle group is shown in FIG. 24 (n=8, mean±SD, *p<0.05 vs. vehicle (t-test)), in which the average of the cerebral infarct size ratios in the vehicle group was taken as 100.

Example 20

Characterization of Polypeptides Contained in Enzyme-Digested, Reverse-Phase Column Fraction of Basic Fraction of Shark Cartilage Extract Twenty-four polypeptides contained in the alcalase-digested, reverse phase column fraction of the basic fraction were synthesized in yields of 10 to 300 mg in the same manner as described in Example 7 and their characteristic values were determined. The molecular weight, solubility, and appearance of the resulting polypeptides are shown in Table 9.

TABLE 9

| Amino Acid Sequence | Mol. | Solubility | Appearance |
|---|---|---|---|
| Tyr-Tyr | 344.4 | 1 mg/ml in water | white lyophilized powder |
| Ser-Leu | 218.3 | 1 mg/ml in water | white lyophilized powder |
| Leu-Tyr | 294.4 | 1 mg/ml in 5% $NH_4OH$ $NH_4OH$ with $H_2O$ | white lyophilized powder |
| Tyr-Phe | 328.4 | 1 mg/ml in 5% $NH_4OH$ $NH_4OH$ with $H_2O$ | white lyophilized powder |
| Phe-Tyr | 328.4 | 1 mg/ml in $H_2O$ | white lyophilized powder |
| Tyr-Leu | 294.4 | 1 mg/ml in $H_2O$ | white lyophilized powder |
| Leu-Phe | 278.4 | 1 mg/ml in $H_2O$ | white lyophilized powder |
| Arg-Tyr-Phe | 484.6 | 1 mg/ml in $H_2O$ | white lyophilized powder |
| Val-Tyr-Gln | 408.5 | 1 mg/ml in $H_2O$ | white lyophilized powder |
| Tyr-Asn-Leu | 408.5 | 1 mg/ml in $H_2O$ | white lyophilized powder |
| Ile-Asn-Tyr | 408.5 | 1 mg/ml in 5% $NH_4OH$ with $H_2O$ | white lyophilized powder |
| Gly-Tyr-Leu | 351.4 | 1 mg/ml in $H_2O$ | white lyophilized powder |
| Gly-Phe-Leu | 335.4 | 1 mg/ml in 10% Acetonitrile in $H_2O$ | white lyophilized powder |
| Ile-Asn-Phe | 392.5 | 1 mg/ml in $H_2O$ | white lyophilized powder |
| Ile-Tyr-Leu | 407.5 | 1 mg/ml in 10% in Acetonitrile water | white lyophilized powder |
| Ser-Asn-Trp-Gln (SEQ ID No: 7) | 533.5 | 1 mg/ml in $H_2O$ | white lyophilized powder |
| Ser-Ile-Tyr-Asp (SEQ ID No: 6) | 496.5 | 1 mg/ml in 5% $NH_4OH$ with water | white lyophilized powder |
| Val-Gln-Tyr-Phe (SEQ ID No: 8) | 556.6 | 1 mg/ml in water | white lyophilized powder |
| Try-Ile-Asn-Tyr (SEQ ID No: 2) | 571.6 | 1 mg/ml in 5% $NH_4OH$ with water | white lyophilized powder |
| Tyr-Leu-Asp-Asn (SEQ ID No: 9) | 523.6 | 1 mg/ml in water | white lyophilized powder |
| Leu-Asp-Asn-Tyr (SEQ ID No: 10) | 523.6 | 1 mg/ml in water | white lyophilized powder |
| Tyr-Leu-Asp-Asn-Tyr (SEQ ID No: 1) | 686.7 | 1 mg/ml in 10% Acetonitrile in water | white lyophilized powder |
| Asp-Phe-Trp-Arg-Tyr (SEQ ID No: 5) | 785.9 | 1 mg/ml in water | white lyophilized powder |
| Ser-Pro-Pro-Tyr-Trp-Pro-Tyr (SEQ ID No: 3) | 909.0 | 1 mg/ml in water | white lyophilized powder |

Example 21

Evaluation of Serum Uric Acid Level Lowering Activity of Polypeptide Having SEQ ID No. 1

A polypeptide having SEQ ID No. 1 (YLDNY) contained in the enzyme-digested reverse phase column fraction of the basic fraction of the shark cartilage extract was synthesized in the same manner as in Example 7 and administered orally to rats at a dose of 5 to 50 mg/kg B.W. One hour later, a single dose of 250 mg/kg B.W. of a 3% gum arabic saline solution of potassium oxonate as a hyperuricemia inducing agent was intraperitoneally administered. After 1 hour from the administration of the hyperuricemia inducing agent, blood was collected from the abdominal aorta under anesthesia with Nembutal. The serum separated from the blood sample in a usual manner was evaluated for serum uric acid level in accordance with the method recommended by Japan Society of Clinical Chemistry (*Clinical Chemistry*, Vol. 22, pp. 300-307, 1993). As a result, serum uric acid level lowering activity was observed, and the 50% inhibitory dose ($ID_{50}$) was calculated to be 39.3 mg/kg. The results of evaluation are shown in FIG. 25 (n=6, mean±SD, *$p<0.05$ vs. 0 mg/kg (Dunnett's test)).

Example 22

Evaluation of Uric Acid Synthetase Inhibitory Activity of Peptide Consisting of Part of SEQ ID No. 1

Peptides YL, LD, DN, NY, YLD, LDN, DNY, YLDN (SEQ ID No: 9), LDNY (SEQ ID No: 10), each of which is a part of the amino acid sequence of the polypeptide having SEQ ID No. 1 (YLDNY) contained in the enzyme-digested reverse-phase column fraction of the basic fraction of a shark cartilage extract, were synthesized in the same manner as in Example 7. Each of the peptides synthesized was added to 1 ml of a 50 mM tris-HCl buffer (pH 7.4) containing 15 μM xanthine as an enzyme substrate to prepare a reaction system. To the reaction system was added 0.1 unit (containing 100 μl of 25 units/25 ml enzyme solution) of xanthine oxidase (XO) of cow's milk (from Wako Pure Chemical), followed by allowing the system to react at 37° C. for 10 minutes. The amount of uric acid produced from xanthine by the action of xanthine oxidase was evaluated in terms of changes in optical density (OD, at 292 nm), from which the enzyme activity was calculated from formula previously given. As a result, xanthine oxidase activity was inhibited in the system containing the peptide LD, DN, LDN, DNY, YLDN (SEQ ID No: 9) or LDNY (SEQ ID No: 10), a part of the amino acid sequence of the polypeptide having SEQ ID No. 1 (YLDNY). The 50% inhibitory concentrations ($IC_{50}$) were calculated to be $1.7 \times 10^{-3}$ M for LD; $5.0 \times 10^{-4}$ M for DN; $7.6 \times 10^{-4}$ M for LDN; $8.8 \times 10^{-4}$ M for DNY; $1.2 \times 10^{-3}$ M for YLDN (SEQ ID No: 9); and $7.5 \times 10^{-4}$ M for LDNY (SEQ ID No: 10). The results obtained are graphically represented in FIGS. 26, 27, and 28 (n=6, mean±SD, *p<0.05 vs. control (Dunnett's test)).

Example 23

Evaluation of Uric Acid Synthetase Inhibitory Activity of Polypeptide Having SEQ ID No. 2

A polypeptide having SEQ ID No. 2 (YINY), which is contained in the enzyme-digested reverse-phase column fraction of the basic fraction of a shark cartilage extract, was synthesized in the same manner as in Example 7 and added to 200 μl of a 50 mM tris-HCl buffer (pH 7.4) containing 15 μM xanthine as an enzyme substrate to prepare a reaction system. To the reaction system was added 0.1 unit (containing 1 μl of 10 units/100 μl enzyme solution) of xanthine oxidase (XO) from butter milk (from Wako Pure Chemical), followed by allowing the system to react at 37° C. for 10 minutes. The amount of uric acid produced from xanthine by the action of xanthine oxidase was evaluated in terms of changes in optical density (OD, at 292 nm), from which the enzyme activity was calculated from formula previously given. As a result, xanthine oxidase activity was inhibited in the system containing the polypeptide having SEQ ID No. 2 (YINY). The 50% inhibitory concentration ($IC_{50}$) was calculated to be $3.7 \times 10^{-3}$ M. The results obtained are shown in FIG. 29 (n=6, mean±SD, *p<0.05 vs. control (Dunnett's test)).

Example 24

Evaluation of Uric Acid Synthetase Inhibitory Activity of Polypeptides Contained in Enzyme-Digested Reverse-Phase Column Fraction of Basic Fraction of Shark Cartilage Extract Polypeptides YNL, GYL, and INF which are contained in the enzyme-digested reverse-phase column fraction of the basic fraction of a shark cartilage extract were synthesized in the same manner as in Example 7 and added to 200 μl of a 50 mM tris-HCl buffer (pH 7.4) containing 15 μM xanthine as an enzyme substrate to prepare a reaction system. To the reaction system was added 0.1 unit (containing 1 μl of 10 units/100 μl enzyme solution) of xanthine oxidase (XO) from butter milk (from Wako Pure Chemical), followed by allowing the system to react at 37° C. for 10 minutes. The amount of uric acid produced from xanthine by the action of xanthine oxidase was evaluated in terms of changes in optical density (OD, at 292 nm), from which the enzyme activity was calculated from formula previously given. As a result, xanthine oxidase activity was inhibited in the system containing the polypeptide YNL, GYL or INF. The results obtained are shown in FIG. 30 (n=6, mean±SD, *p<0.05 vs. control (Dunnett's test)).

INDUSTRIAL APPLICABILITY

The present invention provides a composition useful in the fields of foods, beverages, and pharmaceuticals and applicable to the prevention and treatment of adult diseases including hyperuricemia and to a food, beverage or pharmaceutical preparation containing the composition.

The invention claimed is:

1. A polypeptide composition effective to treat gout or hyperuricemia, comprising as an active ingredient at least one of a polypeptide consisting of the amino acid sequence consisting of SEQ ID NO: 1, a fragment of said polypeptide consisting of four amino acids of SEQ ID NO: 1, or a pharmaceutically acceptable salt thereof.

2. The composition according to claim 1, wherein the active ingredient is a polypeptide consisting of the amino acid sequence of SEQ ID NO: 1 or a pharmaceutically acceptable salt thereof.

3. A food, beverage or pharmaceutical preparation effective to treat gout or hyperuricemia comprising as an active ingredient the polypeptide composition according to claim 1.

4. A method of treating gout or hyperuricemia in a subject, comprising administering the peptide composition of claim 1 to a subject in need thereof.

5. A method of treating gout or hyperuricemia in a subject, comprising administering the food, beverage or pharmaceutical preparation of claim 3 to a subject in need thereof.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Prionace glauca

<400> SEQUENCE: 1

Tyr Leu Asp Asn Tyr
1               5

<210> SEQ ID NO 2
<211> LENGTH: 4
<212> TYPE: PRT
<213> ORGANISM: Prionace glauca

<400> SEQUENCE: 2

Tyr Ile Asn Tyr
1

<210> SEQ ID NO 3
<211> LENGTH: 7
<212> TYPE: PRT
<213> ORGANISM: Prionace glauca

<400> SEQUENCE: 3

Ser Pro Pro Tyr Trp Pro Tyr
```

```
<210> SEQ ID NO 4
<211> LENGTH: 7
<212> TYPE: PRT
<213> ORGANISM: Prionace glauca

<400> SEQUENCE: 4

Ser Leu Pro Tyr Trp Pro Tyr
1               5

<210> SEQ ID NO 5
<211> LENGTH: 5
<212> TYPE: PRT
<213> ORGANISM: Prionace glauca

<400> SEQUENCE: 5

Asp Phe Trp Arg Tyr
1               5

<210> SEQ ID NO 6
<211> LENGTH: 4
<212> TYPE: PRT
<213> ORGANISM: Prionace glauca

<400> SEQUENCE: 6

Ser Ile Tyr Asp
1

<210> SEQ ID NO 7
<211> LENGTH: 4
<212> TYPE: PRT
<213> ORGANISM: Prionace glauca

<400> SEQUENCE: 7

Ser Asn Trp Gln
1

<210> SEQ ID NO 8
<211> LENGTH: 4
<212> TYPE: PRT
<213> ORGANISM: Prionace glauca

<400> SEQUENCE: 8

Val Glu Tyr Phe
1

<210> SEQ ID NO 9
<211> LENGTH: 4
<212> TYPE: PRT
<213> ORGANISM: Prionace glauca

<400> SEQUENCE: 9

Tyr Leu Asp Asn
1

<210> SEQ ID NO 10
<211> LENGTH: 4
<212> TYPE: PRT
<213> ORGANISM: Prionace glauca

<400> SEQUENCE: 10

Leu Asp Asn Tyr
1
```